US011238318B2

(12) United States Patent
Sun et al.

(10) Patent No.: US 11,238,318 B2
(45) Date of Patent: Feb. 1, 2022

(54) METHODS AND APPARATUS FOR HILN CHARACTERIZATION USING CONVOLUTIONAL NEURAL NETWORK

(71) Applicant: Siemens Healthcare Diagnostics Inc., Tarrytown, NY (US)

(72) Inventors: Shanhui Sun, Princeton, NJ (US); Stefan Kluckner, Berlin (DE); Yao-Jen Chang, Princeton, NJ (US); Terrence Chen, Princeton, NJ (US); Benjamin S. Pollack, Jersey City, NJ (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 43 days.

(21) Appl. No.: 16/604,125

(22) PCT Filed: Apr. 10, 2018

(86) PCT No.: PCT/US2018/026936
§ 371 (c)(1),
(2) Date: Oct. 9, 2019

(87) PCT Pub. No.: WO2018/191287
PCT Pub. Date: Oct. 18, 2018

(65) Prior Publication Data
US 2020/0151498 A1 May 14, 2020

Related U.S. Application Data

(60) Provisional application No. 62/485,254, filed on Apr. 13, 2017.

(51) Int. Cl.
*G06K 9/00* (2006.01)
*A61B 5/00* (2006.01)
(Continued)

(52) U.S. Cl.
CPC .......... *G06K 9/628* (2013.01); *G06K 9/2018* (2013.01); *G06K 9/2036* (2013.01);
(Continued)

(58) Field of Classification Search
USPC ....... 382/100, 103, 108, 128–134, 155, 162, 382/168, 173, 181, 191, 199, 209, 219, (Continued)

(56) References Cited

U.S. PATENT DOCUMENTS 10,325,182 B2    6/2019   Soomro et al.
10,685,739 B2 *  6/2020   Tran ..................... G16B 20/20
(Continued)

FOREIGN PATENT DOCUMENTS

JP    2014-504731 A    2/2014
JP    2017-045341 A    3/2017
(Continued)

OTHER PUBLICATIONS

PCT International Search Report and Written Opinion dated Jun. 19, 2018 (12 Pages).
(Continued)

*Primary Examiner* — Seyed H Azarian

(57) ABSTRACT

A method of characterizing a serum and plasma portion of a specimen in regions occluded by one or more labels. The characterization may be used for determining Hemolysis (H), Icterus (I), and/or Lipemia (L), or Normal (N) of a serum or plasma portion of a specimen. The method includes capturing one or more images of a labeled specimen container including a serum or plasma portion, processing the one or more images with a convolutional neural network to provide a determination of Hemolysis (H), Icterus (I), and/or Lipemia (L), or Normal (N). In further embodiments, the convolutional neural network can provide N'-Class segmentation information. Quality check modules and testing appa-
(Continued)

ratus adapted to carry out the method are described, as are other aspects.

19 Claims, 11 Drawing Sheets

(51) Int. Cl.
*G06K 9/62* (2006.01)
*G06K 9/20* (2006.01)
*G06N 3/04* (2006.01)
*G06N 3/08* (2006.01)
*G06T 7/00* (2017.01)

(52) U.S. Cl.
CPC ......... *G06K 9/6217* (2013.01); *G06K 9/6289* (2013.01); *G06N 3/04* (2013.01); *G06N 3/08* (2013.01); *G06T 7/0012* (2013.01); *G06K 2209/05* (2013.01); *G06T 2207/10144* (2013.01); *G06T 2207/10152* (2013.01)

(58) Field of Classification Search
USPC ....... 382/232, 254, 274, 276, 286–293, 305, 382/321, 156; 348/143; 600/328
See application file for complete search history.

(56) References Cited

U.S. PATENT DOCUMENTS

| | | | |
|---|---|---|---|
| 10,746,665 B2 | 8/2020 | Kluckner et al. | |
| 10,746,753 B2 | 8/2020 | Kluckner et al. | |
| 10,816,538 B2 | 10/2020 | Kluckner et al. | |
| 10,824,832 B2 | 11/2020 | Kluckner et al. | |
| 11,022,620 B2 | 6/2021 | Kluckner et al. | |
| 11,035,870 B2 | 6/2021 | Kluckner et al. | |
| 11,042,788 B2 | 6/2021 | Kluckner et al. | |
| 2012/0140230 A1 | 6/2012 | Miller | |
| 2015/0044780 A1 | 2/2015 | Kurz et al. | |
| 2015/0213599 A1 | 7/2015 | Buzaglo et al. | |
| 2015/0241457 A1* | 8/2015 | Miller | G06K 7/1092 348/143 |
| 2016/0334403 A1* | 11/2016 | Gibbons | G01N 21/59 |
| 2016/0349237 A1* | 12/2016 | Klinec | G01N 33/49 |
| 2018/0211380 A1* | 7/2018 | Tandon | G06K 9/6271 |
| 2019/0033209 A1 | 1/2019 | Kluckner et al. | |

FOREIGN PATENT DOCUMENTS

| | | |
|---|---|---|
| JP | 2017-059207 A | 3/2017 |
| WO | 2016/133900 A1 | 8/2016 |

OTHER PUBLICATIONS

Vedaldi et al. "MatConvNet—Convolutional Neural Networks for MATLAB" May 5, 2016 (May 5, 2016) (arXiv:1412.4564v3[cs.CV]) p. 4, para 3; p. 9, para 5; p. 10, para 1.

Paul E. Debevec and Jitendra Malik, "Recovering High Dynamic Range Radiance Maps from Photographs", Proceedings of the 24th annual conference on Computer graphics and interactive techniques (SIGGRAPH '97).

Alex Krizhevsky, Ilya Sutskever, and Geoffrey E. Hinton, "ImageNet Classification with Deep Convolutional Neural Networks", NIPS 2012, pp. 1-9.

Jonathan Long, Evan Shelhamer, and Trevor Darrell, "Fully Convolutional Networks for Semantic Segmentation", CVPR 2015, pp. 3431-3440.

Philipp Krahenbuhl and Vladlen Koltun, "Efficient Inference in Fully Connected CRFs with Gaussian Edge Potentials", NIPS 2011, pp. 1-9.

* cited by examiner

METHODS AND APPARATUS FOR HILN CHARACTERIZATION USING CONVOLUTIONAL NEURAL NETWORK

CROSS-REFERENCE TO RELATED APPLICATIONS

This application claims priority to U.S. provisional application Ser. No. 62/485,254 filed on Apr. 13, 2017, the contents of which is incorporated herein by reference in its entirety.

FIELD

The present disclosure relates to methods and apparatus for characterizing a specimen container and specimen, and, more particularly to methods and apparatus for determining if a specimen includes hemolysis (H), icterus (I), and/or lipemia (L), or is normal (N).

BACKGROUND

Automated testing systems may be used to conduct clinical chemistry or assay testing using one or more reagents to identify an analyte or other constituent in a specimen such as urine, blood serum, blood plasma, interstitial liquid, cerebrospinal liquid, or the like. For convenience and safety reasons, these specimens may be contained within specimen containers (e.g., blood collection tubes). The assay or test reactions generate various changes that can be read and/or manipulated to determine a concentration of analyte or other constituent present in the specimen. Such specimen containers may have one or more labels provided thereon. The label(s) may be a manufacturer's label and/or a label including identifying information aiding in the identification of the specimen and possibly tests to be performed thereon. In most instances, at least one label includes identifying information, such as a barcode (hereinafter a "barcode label"). The label(s) may be made of paper with adhesive backing, for example. In some cases, a gel separator may be added to the specimen container to aid in the separating the settled blood portion from the serum or plasma portion during centrifugation.

Improvements in automated testing technology have been accompanied by corresponding advances in pre-analytical specimen preparation and handling operations such as sorting, batch preparation, centrifuging of specimen containers to separate specimen constituents, cap removal to facilitate specimen access, aliquot preparation, and pre-screening for HILN by automated systems that may be part of a Laboratory Automation System (LAS). The LAS may automatically transport specimens in the specimen containers to one or more pre-analytical specimen processing stations as well as to analyzer stations containing clinical chemistry analyzers and/or assay instruments (hereinafter collectively "analyzers").

These LASs may handle a number of different specimens at one time, and may use the barcode label for tracking and routing. The barcode label may contain a code an accession number that may be correlated to demographic information that may be entered into a hospital's Laboratory Information System (LIS) along with test orders and/or other information, wherein the LIS interfaces with the LAS. An operator may place the labeled specimen containers onto the LAS system, which may automatically route the specimen containers for one or more pre-analytical operations; all of which may be prior to the specimen actually being subjected to clinical analysis or assaying by one or more analyzers that may be part of the LAS.

After fractionation and subsequent pre-analytical processing, the specimen container may be transported to an appropriate analyzer that may extract, via aspiration, serum or plasma portion from the specimen container and combine the serum or plasma portion with one or more reagents in a reaction vessel (e.g., cuvette or other vessel). Analytical measurements may then be performed, often using a beam of interrogating radiation, for example, or by using photometric or fluorometric absorption readings, or the like. The measurements allow determination of end-point or rate values, from which a concentration of analyte or other constituent may be determined using well-known techniques.

Unfortunately, the presence of any interferent (e.g., H, I, and/or L) in the specimen, as a result of a patient condition or sample processing, may possibly adversely affect test results of the analyte or constituent measurement obtained from the one or more analyzers. For example, the presence of hemolysis in the specimen, which may be unrelated to the patient disease state, may cause a different interpretation of the disease condition of the patient. Moreover, the presence of icterus and/or lipemia in the specimen may also cause a different interpretation of the disease condition of the patient.

In some prior art systems, integrity of the serum or plasma portion of the specimen may be visually inspected and rated for a degree of H, I, and/or L (e.g., by assigning an index) or indicating as being normal (N) by a skilled laboratory technician. This may involve a review of the color of the serum or plasma portion against known standards. A normal (N) serum or plasma portion has a light yellow to light amber color. Serum or plasma portion containing hemolysis (H) has a reddish color. Serum or plasma portion containing icterus (I) has a dark yellow color due to increased bilirubin, and serum or plasma portion containing lipemia (L) has a whitish or milky appearance. Depending on the color, the laboratory technician assigns an interferent type and an index value. However, such visual inspection by a person, even of skilled, is very subjective, labor intensive, and fraught with possible human error.

Because manual inspection includes the problems listed above, efforts have been undertaken to evaluate specimen integrity without the use of visual inspection by a laboratory technician, but rather by using an automated, machine-vision inspection apparatus wherein such evaluation takes place during pre-analytical testing (hereinafter "pre-screening"). The pre-screening involves automated detection of an interferent, such as H, I, and/or L, in a serum or plasma portion obtained from whole blood by fractionation (e.g., by centrifugation).

However, in some instances, one or more of the above-described labels may be provided (e.g., adhered) directly to the specimen container. Such label(s) may partially occlude and obscure certain lateral viewpoints of the specimen, so that there may be some orientations that do not provide a clear opportunity to visually observe the serum or plasma portion. Thus, automation of such pre-screening has included, for example, rotationally orienting the specimen in such a way that allows for automated pre-screening for H, I, and/or L or N.

For example, in some systems, such as those described in U.S. Pat. No. 9,322,761 to Miller entitled "Methods And Apparatus For Ascertaining Interferents And Physical Dimensions in Liquid Samples And Containers To Be Analyzed By A Clinical Analyzer" the specimen container is rotated to find a view window that is unobstructed by the label after which the imaging is carried out.

In other systems, such as those described in WO2016/133,900 to Park et al., the specimen container and specimen are imaged from multiple viewpoints and processed with model-based systems so that rotation of the specimen container is not needed.

In some instances, only a small portion of the serum or plasma portion may be visible, so that any H, I, and/or L, or N reading taken on the serum or plasma portion may not involve a high confidence level. Moreover, such systems may be complicated and processing of the image data may be computationally burdensome.

Accordingly, there is an unmet need for a robust and efficient method and apparatus adapted to characterize a serum or plasma portion of a specimen, so as to be able to determine a presence of H, I, and/or L or N.

SUMMARY

According to a first aspect, a characterization method is provided. The characterization method includes capturing multiple images of a specimen container including a serum or plasma portion of a specimen, inputting image data from the multiple images to a convolutional neural network and processing the image data with the convolutional neural network, and outputting from the convolutional neural network: a classification of the serum or plasma portion as being one or more of hemolytic, icteric, lipemic, and normal.

According to another aspect, a quality check module adapted to determine presence of an interferent in a specimen contained within a specimen container is provided. The quality check module includes an image capture device configured to capture multiple images of a specimen container containing a serum or plasma portion of a specimen, and a computer coupled to the image capture device, the computer configured and capable of being operated to: input image data from the multiple images to a convolutional neural network and process the image data with the convolutional neural network, and output from the convolutional neural network a classification of the serum or plasma portion as being one or more of hemolytic, icteric, lipemic, and normal.

In another aspect, a specimen testing apparatus adapted to determine presence of an interferent in a specimen contained within a specimen container is provided. The specimen testing apparatus includes a track, a carrier moveable on the track and configured to contain a specimen container containing a serum or plasma portion of a specimen, image capture devices arranged around the track and configured to capture multiple images of a specimen container and the serum or plasma portion of the specimen from multiple viewpoints, and a computer coupled to the image capture devices, the computer configured and capable of being operated to: input image data from the multiple images to a convolutional neural network and process the image data with the convolutional neural network, and output from the convolutional neural network a classification of the serum or plasma portion as being one or more of hemolytic, icteric, lipemic, and normal.

Still other aspects, features, and advantages of the present disclosure may be readily apparent from the following description by illustrating a number of example embodiments and implementations, including the best mode contemplated for carrying out the present invention. The present invention may also be capable of other and different embodiments, and its several details may be modified in various respects, all without departing from the scope of the present invention. The disclosure is intended to cover all modifications, equivalents, and alternatives falling within the scope of the appended claims.

BRIEF DESCRIPTION OF THE DRAWINGS

The drawings, described below, are for illustrative purposes and are not necessarily drawn to scale. Accordingly, the drawings and descriptions are to be regarded as illustrative in nature, and not as restrictive. The drawings are not intended to limit the scope of the invention in any way.

DETAILED DESCRIPTION

Figure 1:
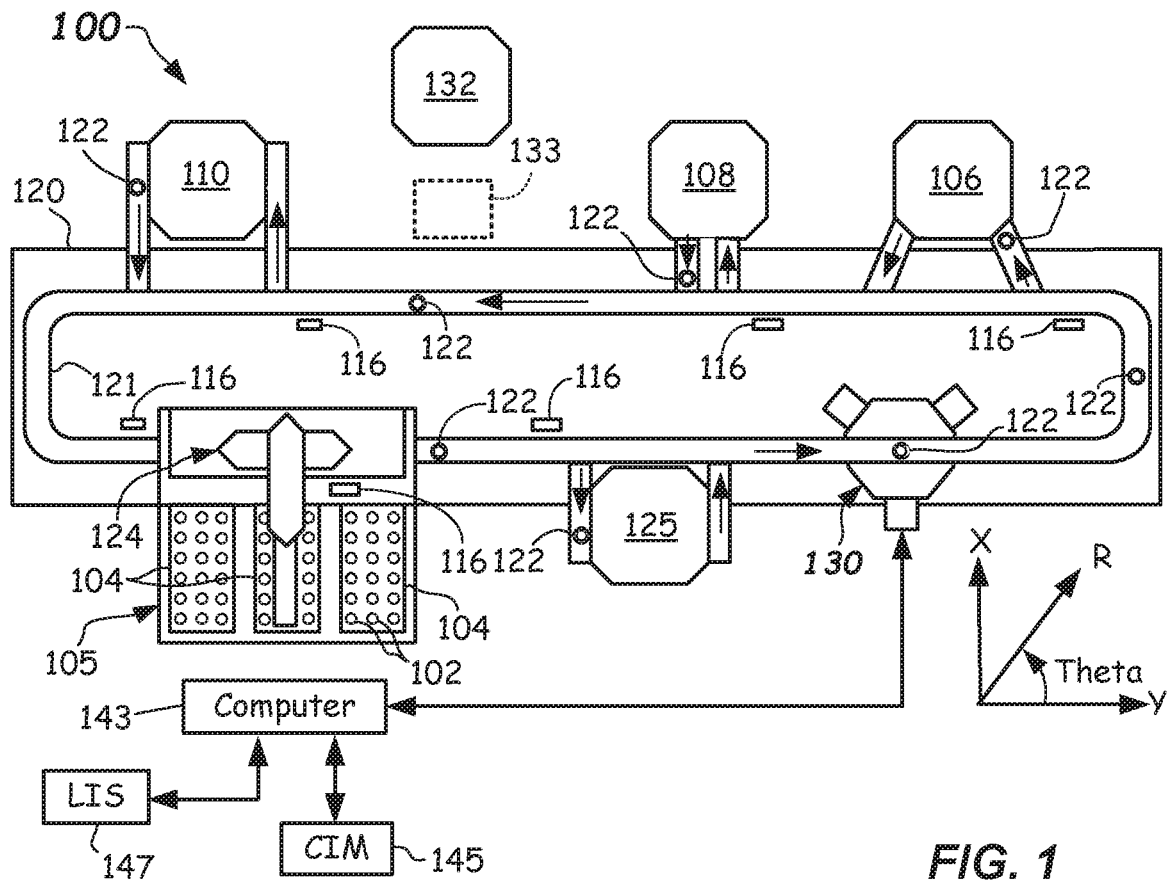
FIG. 1 illustrates a top schematic view of a specimen testing apparatus including one or more quality check modules configured to carry out HILN detection methods according to one or more embodiments.

During pre-analysis characterization (pre-screening) of a specimen contained in a specimen container, such as at a quality check module, a method is provided that determines the presence of an interferent, such as H, I, and/or L, or N (hereinafter "HILN") in the serum or plasma portion. The method may determine just HILN or N-Class H (e.g., H1, H2, H3, or more), N-Class I (e.g., I1, I2, I3, or more), and/or N-Class L (e.g., L1, L2, L3, or more), or N. In addition, the method may classify (hereinafter segmentation") various regions of the specimen container and specimen, such as serum or plasma portion, settled blood portion, gel separator (if used), label, the specimen container (e.g., tube), air, cap. Holder or background may also be classified. Differentiation of the serum and plasma portion from the region comprising one or more labels is a particularly vexing problem because the one or more labels may wrap around the specimen container to various degrees. Thus, the one or more labels may obscure one or more views, such that a clear view of the serum or plasma portion may be difficult to obtain.

Thus, classification of the serum or plasma portion may be quite challenging due to interference from the one or more labels, whose placement may vary substantially from one specimen container to the next being pre-screened. In particular, the obstruction caused by the one or more labels may heavily influence the spectral responses, such as from various viewpoints, given that the one or more labels may appear on a back side and thus affect light transmission received at the front side.

Moreover, it is desired that the quality check module and method be computationally efficient. Accordingly, given the challenges described above, in a first broad aspect, embodiments of the present disclosure provide methods, apparatus, and systems configured to determine the presence of HILN using a convolutional neural network (CNN).

The input to the CNN is multi-spectral, multi-exposure image data, which may be consolidated and normalized, and obtained from one or more image capture devices. The one or more image capture devices may comprise multiple image capture devices arranged and configured to capture images from more than one viewpoint (e.g., three viewpoints). In some embodiments, the CNN is trained to recognize regions occluded by label so that the CNN can better account for the presence of labels on the back side from any viewpoint in characterizing HILN.

As a result, more effective classification of the serum or plasma region may be available in cases where label obstruction is present, and the confidence in the intensity readings for those regions of the serum or plasma portion that are occluded by label can be improved. Thus, an improved determination of HILN and/or and the extent of HIL can be output from the CNN.

In accordance with one aspect, the characterization method can be carried out by a quality check module, and in specimen testing systems, including the convolutional neural network (CNN). The CNN may include layers including convolution and pooling to extract features, such as simple edges, texture, and parts of the serum or plasma portion and label-containing regions. Top layers, such as fully convolutional layers, may be used to provide correlation between parts. The output of the last connected layer may be fed to a deconvolution layer and SoftMax layer, which produces an output on a per pixel (or per patch—including n×n pixels) basis concerning whether each pixel or patch includes HILN. In some embodiments, only an output of HILN is provided from the CNN. In other embodiments, the output of the CNN may be fin-grained HILN, such as H1, H2, H3, I1, I2, I3, L1, L2, L3, or N, so that for each interferent present an estimate of the level (index) of the interferent is also obtained.

In other embodiments, combination of segmentation output and HILN output may be provided. The outputs may result from multiple branches of the CNN. The branches may include separate convolutional layers and deconvolution and SoftMax layers, wherein one branch may be dedicated to segmentation and the other to HILN detection. Multi-branch embodiments including HILN, segmentation, and cap type detection may also be provided.

Definitions

"Interferent," as used herein, means the presence of at least one of hemolysis (H), icterus (I), or lipemia (L) in the serum or plasma portion of the specimen. Hemolysis (H), icterus (I), and lipemia (L) are collectively referred to as "HIL" herein.

"Hemolysis" is defined as a condition in the serum or plasma portion wherein during processing red blood cells are destroyed, which leads to the release of hemoglobin from the red blood cells into the serum or plasma portion such that the serum or plasma portion takes on a reddish hue. The degree of Hemolysis may be quantified by assigning a Hemolytic Index.

"Icterus" is defined as a condition of the blood where the serum or plasma portion is discolored dark yellow caused by an accumulation of bile pigment (bilirubin). The degree of Icterus may be quantified by assigning an Icteric Index.

"Lipemia" is defined as a presence in the blood of an abnormally high concentration of emulsified fat, such that the serum or plasma portion includes a whitish or milky appearance. The degree of lipemia may be quantified by assigning a Lipemic Index.

"Normal" is defined as serum or plasma portion that includes acceptably low amounts of H, I, and L.

"Serum or plasma portion" is the liquid component of blood. It is found above the settled blood portion after fractionation (e.g., by centrifugation). Plasma and serum differ in the content of coagulating components, primarily fibrinogen. Plasma is the un-clotted liquid, whereas serum refers to blood plasma, which has been allowed to clot either under the influence of endogenous enzymes or exogenous components.

"Settled blood portion" is a packed semi-solid made up blood cells such as white blood cells (leukocytes), red blood cells (erythrocytes), and platelets (thrombocytes), which are aggregated and separated from the serum or plasma portion. The settled blood portion is found at a bottom part of the specimen container below the serum or plasma portion after fractionation.

"Image capture device" is any device capable of capturing a pixelated image (e.g., digital image) for analysis, such as a digital camera, a CCD (charge-coupled device) and CMOS (complementary metal-oxide semiconductor), an array of sensors, or the like.

"Pixelated image" as used herein means images including either single pixels or a grouping of pixels, such as a super-pixel or image patch (patch) including more than one pixel.

"Label" is defined as an area on an outside surface of the specimen container adapted to contain identification information (i.e., indicia). The label may be an opaque paper, plastic, paint, or other material applied (e.g., adhered) to an outer surface of the specimen container. Indicia may be a barcode, alphabetic characters, numeric characters, or combinations thereof. The label may be manufacturer label or may be a label after-applied by a phlebotomist or by a subsequent specimen processing entity that may include a barcode.

"LA" is defined as the liquid-air interface and is a line of demarcation (viewed laterally) between the serum or plasma portion and the air above the serum or plasma portion.

"SB" is the serum-blood interface, which is a line of demarcation (viewed laterally) between the serum or plasma portion and the settled blood portion.

"TC" is the tube-cap interface, which is a line of demarcation (viewed laterally) at the interface between the air and the cap.

"HT" is the height of the tube and is defined as the height from the bottom-most part of the tube to the bottom of the cap.

"HSP," in cases where no gel separator is used, is the height of the serum or plasma portion and is defined as the height from the top of the serum or plasma portion from the top of the settled blood portion, i.e., from LA to SB.

Figure 2:
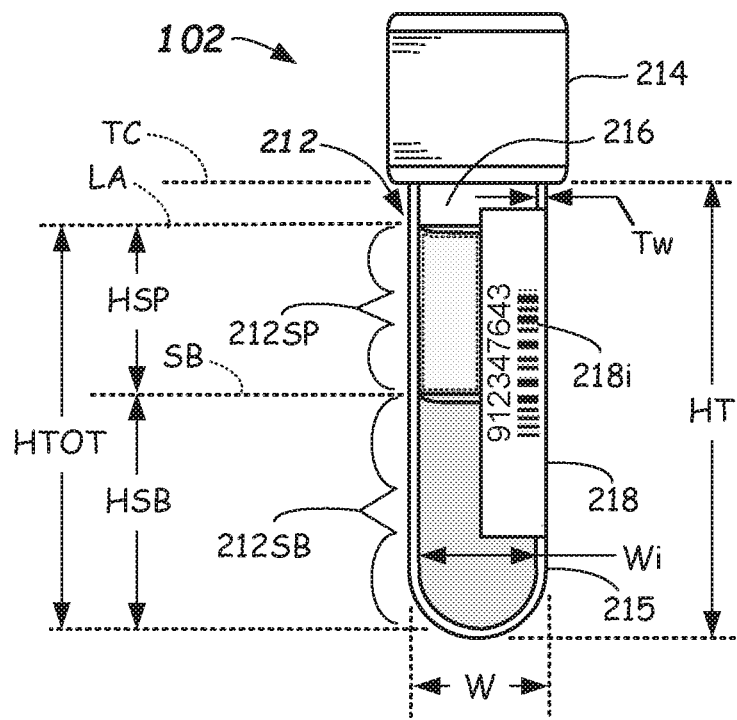
FIG. 2 illustrates a side view of a specimen container including a separated specimen with a serum or plasma portion containing an interferent, and wherein the specimen container includes a label thereon.
Figures 3A, 3B:
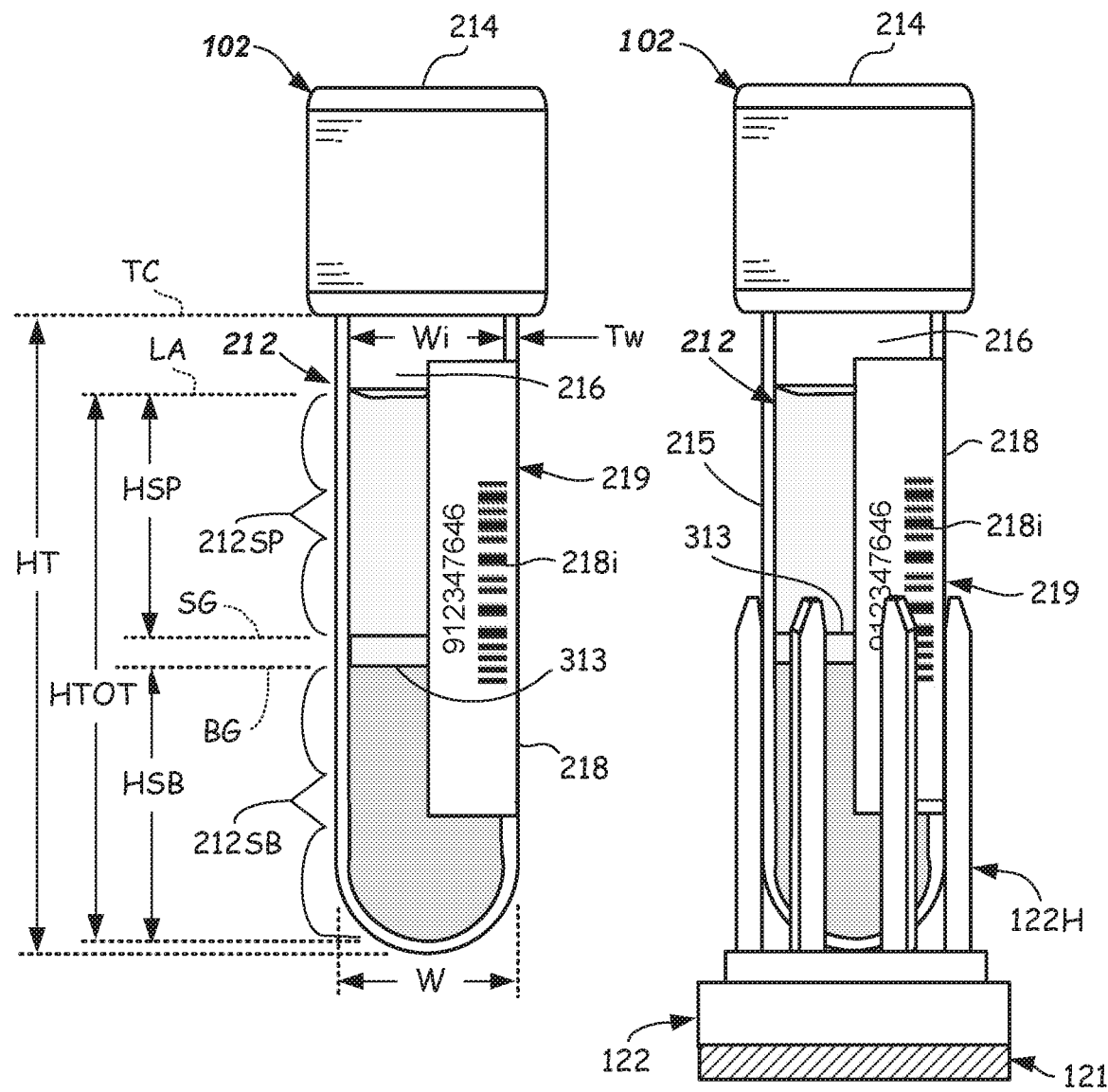
FIG. 3A illustrates a side view of a specimen container including a label, a separated specimen including a serum or plasma portion containing an interferent, and a gel separator therein.
FIG. 3B illustrates a side view of a specimen container including a label, a separated specimen containing an interferent in the serum or plasma portion, a gel separator, and wherein the specimen container is shown being held in an upright orientation in a holder.

"HSP," in cases where a gel separator is used (FIG. 2B), is the height of the serum or plasma portion and is defined as the height from the top of the serum or plasma portion at LA to the top of the gel separator at SG, i.e., from LA to SG.

"HSB," in cases where no gel separator is used, is the height of the settled blood portion and is defined as the height from the bottom of the settled blood portion to the top of the settled blood portion at SB.

"HSB," in cases where a gel separator is used, is the height of the settled blood portion and is defined as the height from the bottom of the settled blood portion to the bottom of the gel separator at BG.

"HTOT," in cases where there is no gel separator is used, is the total height of the specimen and equals HSP+HSB.

"HTOT," in cases where a gel separator is used, is a total height of the specimen, and equals HSP+HSB+height of the gel separator.

"Tw" is the wall thickness of the specimen container.

"W" is an outer width of the specimen container.

"Wi" is an inner width of the specimen container.

"Carrier" is a device that is configured to support and transport a specimen container, such as within a laboratory automation system (LAS).

"VSP" is a volume of the serum or plasma portion in the specimen container.

"VSB" is a volume of the settled blood portion in the specimen container.

"Hemolytic index" as used herein means a grade given to a particular specimen based upon the determined content (degree or amount) of hemolysis present in the serum or plasma portion.

"Icteric index" as used herein means the grade given to a particular specimen based upon a determined content (degree or amount) of icterus present in the serum or plasma portion.

"Lipemic index" as used herein means the grade given to a serum or plasma portion based upon the determined content (degree or amount) of lipemia present in the serum or plasma portion.

"Convolution" as used herein means a processing step that learns and applies filter kernels. During a forward pass, the filter is applied to the input image data by computing a dot product. This results in an activation map of that filter. Thus, the network learns filters that activate when the processing detects some specific type of feature at some spatial position in the input image data.

"Pooling" as used herein means a processing step that performs nonlinear down sampling. Typically, max pooling is applied. Max pooling is achieved by applying a max filter to non-overlapping sub-regions of the representation.

"Deconvolution" as used herein means a reverse convolution. Deconvolution corresponds to a learned upsampling step towards a target image dimension.

"SoftMax" as used herein is a loss that is used for predicting a single class of N mutually exclusive classes.

"ReLU" as used herein means a rectified linear unit and is a processing step that applies an activation function without saturation. A ReLU increases nonlinear properties of the decision function and of the overall CNN without affecting the receptive fields of the particular convolution layer.

"LRN" as used herein means local response normalization and is a processing step that implements a lateral inhibition. This LRN layer is useful when a ReLU is used in order to overcome unbounded activations. Thus, using an LRN, normalization is applied.

The presence of one or more interferent (H, I, and/or L) in the serum or plasma portion, as discussed above, may affect the interpretation of results of the subsequent testing by the one or more analyzers (e.g. clinical chemistry or assay testing). Thus, the ability to pre-screen for HILN, such as at the first possible instance after centrifugation and before analysis by one or more analyzers may advantageously minimize wasted time analyzing specimens that are not of the proper quality for analysis, may avoid or minimize erroneous test results, may minimize patient test result delay, and may avoid wasting of patient specimen. Moreover, in one or more embodiments, remedial action can take place after pre-screening where H, I, and/or L are found in the specimen.

The specimen, as described herein, may be collected in a specimen container, such as a blood collection tube and may include a settled blood portion and a serum and plasma portion after fractionation (e.g., separation by centrifugation). In some specimen containers, a gel separator may be used, which positions itself between the settled blood portion and the serum or plasma portion during centrifugation. The gel separator serves as a physical barrier between the two portions (liquid and semi-solid, settled blood cells), and may minimize remixing thereof. The specimen containers may be of different sizes and thus may be supplied for pre-screening and to the analyzers in a number of different configurations. For example, the specimen containers may have sizes such as 13 mm×75 mm, 13 mm×100 mm, 16 mm×100 mm, and 16 mm×125 mm, for example. Other suitable sizes may be used.

In accordance with one or more embodiments, the characterization method including a CNN may provide a more detailed characterization of the one or more labels. Thus, in one aspect, the improved characterization method provides better characterization of the serum or plasma portion that is occluded by the label-containing region. Thus, the method may provide better classification of the serum or plasma portion in regions where the backlight is obscured by the label(s). Thus, improved interferent detection may be provided. The methods use high dynamic range (HDR) image processing of the specimen container and serum or plasma portion as an input to the CNN. HDR imaging involves capturing multiple exposures while using multiple spectral illuminations.

In one or more embodiments, a quality check module may be configured to carry out the characterization methods. The quality check module may be provided in any suitable area where a robotic mechanism (e.g., a gripper-finger robot) or a track may facilitate transport of specimen containers thereto. In some embodiments, the quality check module may be provided on or along a track of a specimen testing apparatus. The track carries the specimens to the pre-screening locations and to one or more remote locations for analysis (e.g., clinical chemistry testing or assaying) on an analyzer if pre-screening of the specimen determines it to be normal (N).

In some embodiments, the quality check module may be provided directly on the track so that the testing for the presence of an interferent (testing for HILN) can be accomplished while being resident on the track. In embodiments, the specimen container may be held in an upright position by a specimen container holder (hereinafter "holder"). The holder may include fingers or other suitable articles that hold the specimen container during capture of the images. The holder may be part of the carrier in some embodiments.

Should the specimen be found to contain one or more of H, I, and L, a suitable notice may be provided to the operator, and/or may be taken off line to perform a remediation to rectify the one or more of H, I, or L, for further quantification of H, I, or L to more accurately measure an extent of the interferent present, for a redraw, or for other processing.

The methods described herein are image based, i.e., based on pixelated images (e.g., digital images). The images may be obtained, in some embodiments, by multiple image capture devices located so as to capture images from multiple viewpoints (e.g., multiple lateral viewpoints). The multiple images may be obtained at the quality check module, and may be captured at multiple exposures (e.g., exposure times) while providing illumination (e.g., backlighting) at multiple spectra having different nominal wavelengths. The multiple spectra of illumination may include emitted lighting of red (R), green (G), blue (B), white (W), IR and near IR (NIR), for example. In some embodiments, only R, G, and B light sources are used. The illumination may include backlit illumination wherein the image capture device is located on one side and the backlight source is on an opposite side of the specimen container. The exposure time may be varied based upon the lighting intensity and spectrum used and features of the image capture device. Multiple exposure times (e.g., 4-8 different exposures) may be used for each spectrum and for each image capture device (for each viewpoint).

In a pre-processing operation, for each corresponding pixel (or patch, if patch-wise processing) of the multiple captured images at a particular spectrum (at different exposure times), pixels (or patches) exhibiting optimal image intensity may be selected. These selected pixels (or patches) exhibiting optimal image intensity may also be normalized. The result may be a plurality of consolidated and normalized color image data sets, one image data set for each different spectrum of illumination (e.g., R, G, B, W, IR, and/or NIR) and for each viewpoint. These data sets may be provided in the form of data matrices as layers and are operated on by the CNN to determine HILN. In some embodiments, just a determination of HILN is provided as output from the CNN. In other embodiments, the output is an N-class HILN (e.g., a 3-class HILN). In further embodiments, combinations of HILN and segmentation may be output from the CNN. The segmentation may determine pixels or patches classified as serum or plasma portion, as well as other classes (e.g., settled blood portion, label, gel separator, tube, cap, and/or air).

In HILN detection, the CNN may output per pixel data (or per patch) data on the classes of HILN. This data may be output as a histogram and used to determine an overall characterization of the serum or plasma portion as HILN. The data that is output on a per-pixel (or per-patch) basis may be aggregated by any suitable means to determine an overall determination of HILN of the serum or plasma portion. The HILN output may be used for making further decisions, such as rejecting a specimen, providing further processing of the specimen, calling for a redraw of the specimen, providing an indication of the level of uncertainty in the HILN characterization, and the like.

As discussed above, the presence of the one or more labels on the specimen container can affect the intensity values of the image(s) captured. For example, a presence of a label located on the back side of the specimen container from one viewpoint may obscure the back light that can pass through the serum or plasma portion and thus affect the image intensity that is being measured by the image capture device at that viewpoint. Embodiments of the present disclosure including CNN for processing image data account for the presence of such label(s) by being pre-trained to recognize occluded regions. Thus, embodiments of the present disclosure provide for a better and more accurate assessment of the image intensity for the serum or plasma portion from areas where label occlusion has occurred in that selected viewpoint. From this improved characterization, a more accurate determination of HILN may be provided.

Moreover, based upon the more accurate characterization of the serum or plasma portion, an improved determination of interferent type and/or interferent level (interferent index) may be provided in some embodiments. In some embodiments, the CNN may output the interferent level (index). For example, a fine-grained N-Class output may include interferent type and also some measure of interferent level. For example, three levels of hemolysis index may be possible outcomes from the CNN (e.g., H1, H2, H3, or the like). Likewise, icterus index and lipemia index may have three levels of possible outcomes from the CNN (e.g., I1, I2, I3 and L1, L2, and L3). Other numbers of interferent levels may be provided.

Further details of inventive characterization methods, quality check modules configured to carry out the characterization methods, and specimen testing apparatus including one or more quality check modules will be further described with reference to FIGS. 1-7 herein.

FIG. 1 illustrates a specimen testing apparatus 100 capable of automatically processing multiple specimen containers 102 (e.g., see FIGS. 2-3B) containing specimens 212. The specimen containers 102 may be provided in one or more racks 104 at a loading area 105 prior to transportation to, and analysis by, one or more analyzers (e.g., first, second, and third analyzer 106, 108, and/or 110, respectively) arranged about the specimen testing apparatus 100. More or less numbers of analyzers can be used. The analyzers may be any combination of clinical chemistry analyzers and/or assaying instruments, or the like. The specimen containers 102 may be any suitably transparent or translucent container, such as a blood collection tube, test tube, sample cup, cuvette, or other clear or opaque glass or plastic container capable of containing and allowing imaging of the specimen 212 contained therein. The specimen containers 102 may be varied in size.

Specimens 212 (FIGS. 2-3B) may be provided to the specimen testing apparatus 100 in the specimen containers 102, which may be capped with a cap 214. The caps 214 may have different types (e.g., red, royal blue, light blue, green, grey, tan, yellow, or color combinations), which may have meaning in terms of what test the specimen container 102 is used for, the type of additive included therein, whether the container includes a gel separator, or the like. Other colors may be used. In one embodiment, the cap type may be determined by the characterization method described herein.

Each of the specimen containers 102 may be provided with a label 218 which may include identification information 218i (i.e., indicia) thereon, such as a barcode, alphabetic, numeric, or combination thereof. The identification information 218i may be machine readable at various locations about the specimen testing apparatus 100. The machine readable information may be darker (e.g., black) than the label material (e.g., white paper) so that it can be readily imaged. The identification information 218i may indicate, or may otherwise be correlated, via a Laboratory Information System (LIS) 147, to a patient's identification as well as tests to be accomplished upon the specimen 212, or other information, for example. Such identification information 218i may be provided on the label 218 that may be adhered to or otherwise provided on an outside surface of the tube 215. In the depicted embodiment of FIG. 2, the label 218 may not extend all the way around the specimen container 102, or all along a length of the specimen container 102 and from the particular front viewpoint shown, a large part of the serum or plasma portion 212SP is viewable (the part shown dotted) and is unobstructed by the label 218.

However, in some embodiments, multiple labels 218 may have been provided (such as from multiple facilities that have handled the specimen container 102), and they may overlap each other to some extent. For example, two labels (e.g., a manufacturer's label and a barcode label) may be provided and may be overlapping and may occlude (obstruct) some or all of one or more viewpoints.

Thus, it should be understood that in some embodiments, although the label(s) 218 may occlude some portion of the specimen 212 (occluded portion), some portion of the specimen 212 and serum and plasma portion 212SP may still be viewable from at least one viewpoint (un-occluded portion). Thus, in accordance with another aspect of the disclosure, embodiments of the CNN configured to carry out the characterization method can be trained to recognize the occluded and un-occluded portions, such that improved HILN detection may be provided.

Again referring to FIG. 2, the specimen 212 may include the serum or plasma portion 212SP and a settled blood portion 212SB contained within the tube 215. Air 216 may be provided above the serum and plasma portion 212SP and a line of demarcation between them is defined as the liquid-air interface (LA). The line of demarcation between the serum or plasma portion 212SP and the settled blood portion 212SB is defined as a serum-blood interface (SB). An interface between the air 216 and cap 214 is defined as a tube-cap interface (TC). The height of the tube (HT) is defined as a height from a bottom-most part of the tube 215 to a bottom of the cap 214, and may be used for determining tube size. A height of the serum or plasma portion 212SP is (HSP) and is defined as a height from a top of the serum or plasma portion 212SP from a top of the settled blood portion 212SB. A height of the settled blood portion 212SB is (HSB) and is defined as a height from the bottom of the settled blood portion 212SB to a top of the settled blood portion 212SB at SB. HTOT is a total height of the specimen 212 and equals HSP plus HSB.

In cases where a gel separator 313 is used (FIG. 3A), the height of the serum or plasma portion 212SP is (HSP) and is defined as a height from atop of the serum or plasma portion 212SP at LA to the top of the gel separator 313 at SG, wherein SG is an interface between the serum or plasma portion 212SP and the gel separator 313. A height of the settled blood portion 212SB is (HSB) and is defined as a height from the bottom of the settled blood portion 212SB to the bottom of the gel separator 313 at BG, wherein BG is an interface between the settled blood portion 212SB and the gel separator 313. HTOT is the total height of the specimen 212 and equals HSP plus HSB plus height of the gel separator 313. In each case, Tw is a wall thickness, W is an outer width, which may also be used for determining the size of the specimen container 102, and Wi is an inner width of the specimen container 102.

In more detail, specimen testing apparatus 100 may include a base 120 (e.g., a frame, floor, or other structure) upon which a track 121 may be mounted. The track 121 may be a railed track (e.g., a mono rail or a multiple rail), a collection of conveyor belts, conveyor chains, moveable platforms, or any other suitable type of conveyance mechanism. Track 121 may be circular or any other suitable shape and may be a closed track (e.g., endless track) in some embodiments. Track 121 may, in operation, transport individual ones of the specimen containers 102 to various locations spaced about the track 121 in carriers 122.

Carriers 122 may be passive, non-motored pucks that may be configured to carry a single specimen container 102 on the track 121, or optionally, an automated carrier including an onboard drive motor, such as a linear motor that is programmed to move about the track 121 and stop at pre-programmed locations. Other configurations of carrier 122 may be used. Carriers 122 may each include a holder 122H (FIG. 3B) configured to hold the specimen container 102 in a defined upright position and orientation. The holder 122H may include a plurality of fingers or leaf springs that secure the specimen container 102 on the carrier 122, but some may be moveable or flexible to accommodate different sizes of the specimen containers 102. In some embodiments, carriers 122 may leave from the loading area 105 after being offloaded from the one or more racks 104. The loading area 105 may serve a dual function of also allowing reloading of the specimen containers 102 from the carriers 122 to the loading area 105 after pre-screening and/or analysis is completed.

A robot 124 may be provided at the loading area 105 and may be configured to grasp the specimen containers 102 from the one or more racks 104 and load the specimen containers 102 onto the carriers 122, such as onto an input lane of the track 121. Robot 124 may also be configured to reload specimen containers 102 from the carriers 122 to the one or more racks 104. The robot 124 may include one or more (e.g., least two) robot arms or components capable of X (lateral) and Z (vertical—out of the paper, as shown), Y and Z, X, Y, and Z, or r (radial) and theta (rotational) motion. Robot 124 may be a gantry robot, an articulated robot, an R-theta robot, or other suitable robot wherein the robot 124 may be equipped with robotic gripper fingers oriented, sized, and configured to pick up and place the specimen containers 102.

Upon being loaded onto track 121, the specimen containers 102 carried by carriers 122 may progress to a first pre-processing station 125. For example, the first pre-processing station 125 may be an automated centrifuge configured to carry out fractionation of the specimen 212. Carriers 122 carrying specimen containers 102 may be diverted to the first pre-processing station 125 by inflow lane or other suitable robot. After being centrifuged, the specimen containers 102 may exit on outflow lane, or otherwise be removed by a robot, and continue along the track 121. In the depicted embodiment, the specimen container 102 in carrier 122 may next be transported to a quality check module 130 to carry out pre-screening, as will be further described herein with reference to FIGS. 4A-7 herein.

The quality check module 130 is configured to pre-screen and carry out the characterization methods described herein, and is configured to automatically determine a presence of, and possibly an extent of H, I, and/or L contained in a specimen 212 or whether the specimen is normal (N). If found to contain effectively-low amounts of H, I and/or L, so as to be considered normal (N), the specimen 212 may continue on the track 121 and then may be analyzed by the one or more analyzers (e.g., first, second, and/or third analyzers 106, 108, and/or 110). Thereafter, the specimen container 102 may be returned to the loading area 105 for reloading to the one or more racks 104.

In some embodiments, in addition to detection of HILN, segmentation of the specimen container 102 and specimen 212 may take place. From the segmentation data, post processing may be used for quantification of the specimen 212 (i.e., determination of HSP, HSB, HTOT, and determination of location of SB or SG, and LA). In some embodiments, characterization of the physical attributes (e.g., size) of the specimen container 102 may take place at the quality check module 130. Such characterization may include determining HT and W, and possibly TC, and/or Wi. From this characterization, the size of the specimen container 102 may be extracted. Moreover, in some embodiments, the quality check module 130 may also determine cap type, which may be used as a safety check and may catch if a wrong tube type has been used for the test ordered.

In some embodiments, a remote station 132 may be provided on the specimen testing apparatus 100 that is not directly linked to the track 121. For instance, an independent robot 133 (shown dotted) may carry specimen containers 102 containing specimens 212 to the remote station 132 and return them after testing/pre-processing. Optionally, the specimen containers 102 may be manually removed and returned. Remote station 132 may be used to test for certain constituents, such as a hemolysis level, or may be used for further processing, such as to lower a lipemia level through one or more additions and/or through additional processing, or to remove a clot, bubble or foam, for example. Other pre-screening using the HILN detection methods described herein may be accomplished at remote station 132.

Additional station(s) may be provided at one or more locations on or along the track 121. The additional station(s) may include a de-capping station, aliquoting station, one or more additional quality check modules 130, and the like.

The specimen testing apparatus 100 may include a number of sensors 116 at one or more locations around the track 121. Sensors 116 may be used to detect a location of specimen containers 102 on the track 121 by means of reading the identification information 218i, or like information (not shown) provided on each carrier 122. Any suitable means for tracking the location may be used, such as proximity sensors. All of the sensors 116 may interface with the computer 143, so that the location of each specimen container 102 may be known at all times.

The pre-processing stations and the analyzers 106, 108, 110 may be equipped with robotic mechanisms and/or inflow lanes configured to remove carriers 122 from the track 121, and robotic mechanisms and/or outflow lanes configured to reenter carriers 122 to the track 121.

Specimen testing apparatus 100 may be controlled by the computer 143, which may be a microprocessor-based central processing unit CPU, having a suitable memory and suitable conditioning electronics and drivers for operating the various system components. Computer 143 may be housed as part of, or separate from, the base 120 of the specimen testing apparatus 100. The computer 143 may operate to control movement of the carriers 122 to and from the loading area 105, motion about the track 121, motion to and from the first pre-processing station 125 as well as operation of the first pre-processing station 125 (e.g., centrifuge), motion to and from the quality check module 130 as well as operation of the quality check module 130, and motion to and from each analyzer 106, 108, 110 as well as operation of each analyzer 106, 108, 110 for carrying out the various types of testing (e.g., assay or clinical chemistry).

For all but the quality check module 130, the computer 143 may control the specimen testing apparatus 100 according to software, firmware, and/or hardware commands or circuits such as those used on the Dimension® clinical chemistry analyzer sold by Siemens Healthcare Diagnostics Inc. of Tarrytown, N.Y., and such control is typical to those skilled in the art of computer-based electromechanical control programming and will not be further described herein. However, other suitable systems for controlling the specimen testing apparatus 100 may be used. The control of the quality check module 130 may also be provided by the computer 143, but according to the inventive characterization methods described in detail herein.

The computer 143 used for image processing carried out for the characterization methods described herein may include a CPU or GPU, sufficient processing capability and RAM, and suitable storage. In one example, the computer 143 may be a multi-processor-equipped PC with one or more GPUs, 8 GB Ram or more, and a Terabyte or more of storage. In another example, the computer 143 may be a GPU-equipped PC, or optionally a CPU-equipped PC operated in a parallelized mode. MKL could be used as well, 8 GB RAM or more, and suitable storage.

Embodiments of the disclosure may be implemented using a computer interface module (CIM) 145 that allows for a user to easily and quickly access a variety of control and status display screens. These control and status display screens may display and enable control of some or all aspects of a plurality of interrelated automated devices used for preparation and analysis of specimens 212. The CIM 145 may be employed to provide information about the operational status of a plurality of interrelated automated devices as well as information describing the location of any specimen 212 as well as a status of tests to be performed on, or being performed on, the specimen 212. The CIM 145 is thus adapted to facilitate interactions between an operator and the specimen testing apparatus 100. The CIM 145 may include a display screen adapted to display a menu including icons, scroll bars, boxes, and buttons through which the operator may interface with the specimen testing apparatus 100. The menu may comprise a number of function elements programmed to display and/or operate functional aspects of the specimen testing apparatus 100.

Figure 4A:
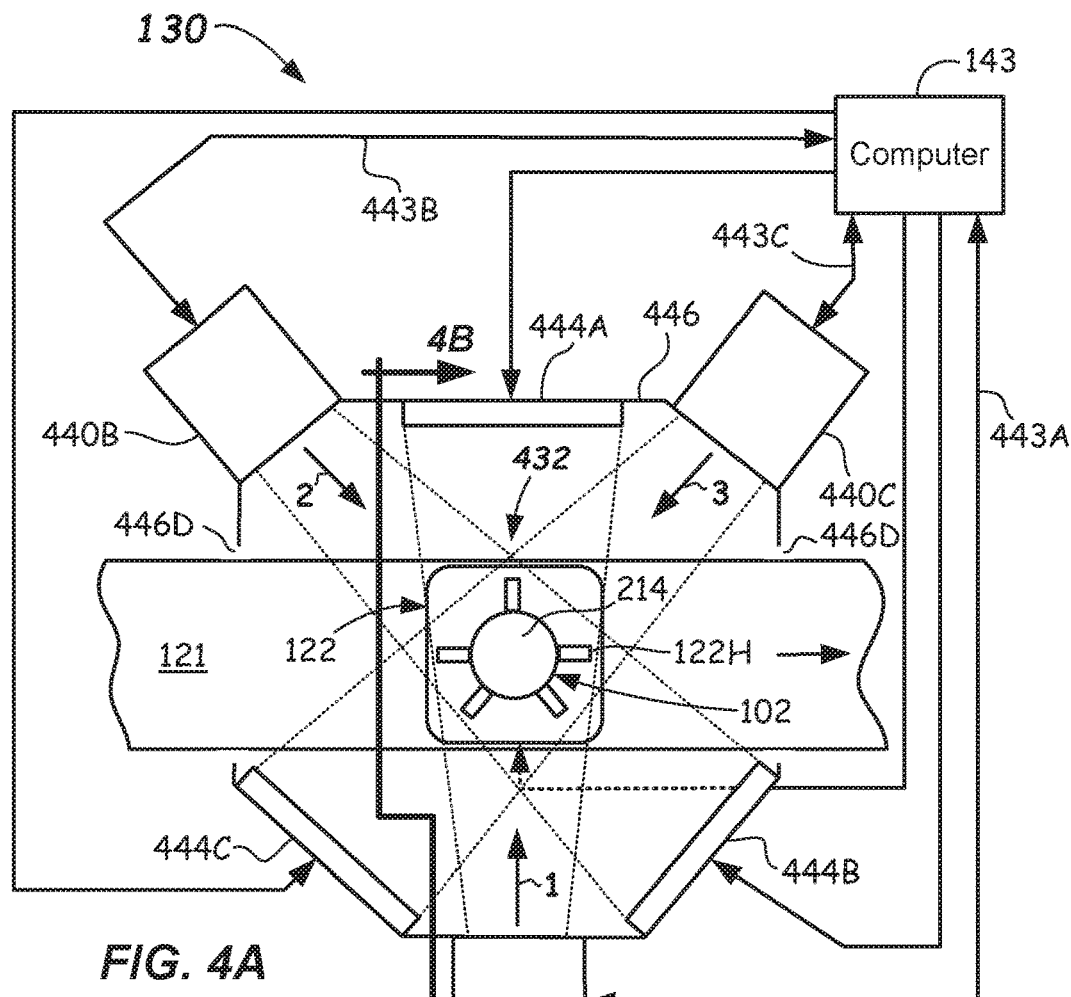
FIG. 4A illustrates a schematic top view of a quality check module (with ceiling removed) including multiple viewpoints and configured to capture and analyze multiple backlit images to enable determining a presence of an interferent according to one or more embodiments.
Figure 4B:
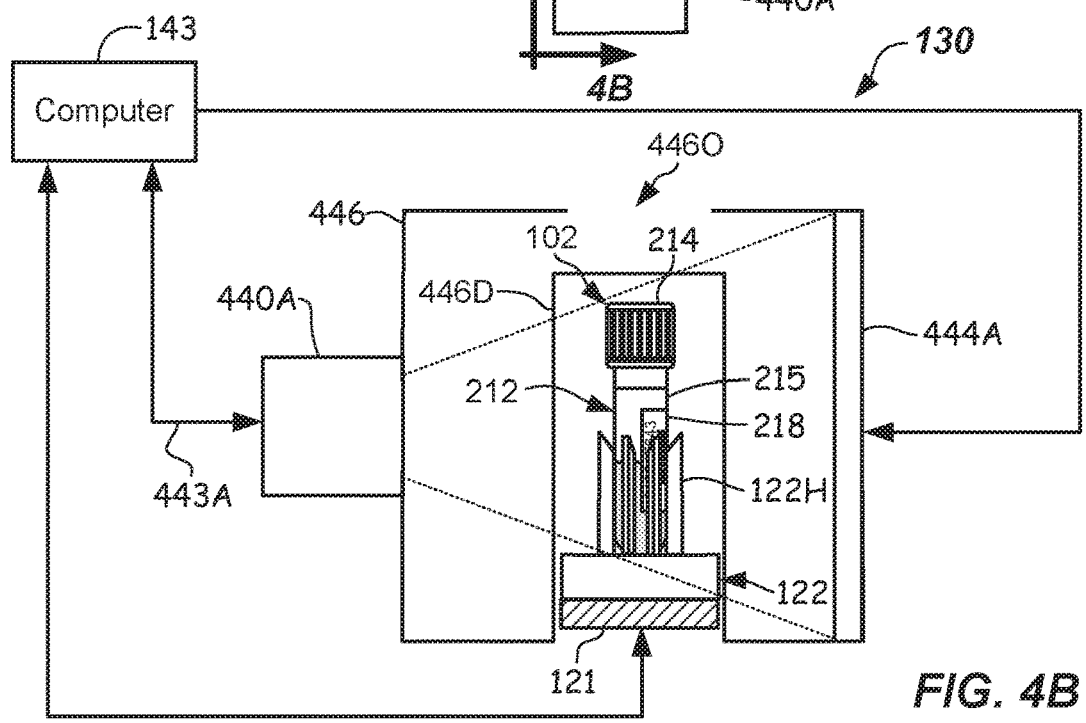
FIG. 4B illustrates a schematic side view of the quality check module (with front enclosure wall removed) of FIG. 4A taken along section line 4B-4B of FIG. 4A according to one or more embodiments.

With reference to FIGS. 4A-4B, a first embodiment of a quality check module 130 configured to carry out the characterization methods is shown and described. Quality check module 130 may be configured and adapted to pre-screen for a presence of an interferent (e.g., H, I, and/or L) in a specimen 212 (e.g., in a serum or plasma portion 212SP thereof) prior to analysis by the one or more analyzers 106, 108, 110. Pre-screening in this manner allows for additional processing, additional quantification or characterization, discarding, and/or redraw of a specimen 212 without wasting valuable analyzer resources or possibly having the presence of an interferent affect the veracity of the test results.

In addition to the interferent detection methods described herein, other detection methods may take place on the specimen 212 contained in the specimen container 102 at the quality check module 130. For example, a method may be carried out at the quality check module 130 to provide segmentation as an output from the CNN. The segmentation data may be used in a post processing step to quantify the specimen 212, i.e., determine certain physical dimensional characteristics of the specimen 212 (e.g., LA and SB, and/or determination of HSP, HSB, and/or HTOT). Quantification may also involve estimating a volume of the serum or plasma portion (VSP) and/or a volume of the settled blood portion (VSB), for example. Other quantifiable geometrical features may also be determined.

Furthermore, the quality check module 130 may be used to quantify geometry of the specimen container 102, i.e., quantify certain physical dimensional characteristics of the specimen container 102, such as the location of TC, HT, and/or W or Wi of the specimen container 102.

Now referring to FIGS. 1, 4A, and 4B, a first embodiment of a quality check module 130 is show including multiple image capture devices 440A-440C. Three image capture devices 440A-440C are shown and are preferred, but optionally two or more or four or more can be used. Image capture devices 440A-440C may be any suitable device for capturing well-defined digital images, such as conventional digital cameras capable of capturing a pixelated image, charged coupled devices (CCD), an array of photodetectors, one or more CMOS sensors, or the like. For example, the three image capture devices 440A, 440B, 440C are illustrated in FIG. 4A and are configured to capture images from three different lateral viewpoints (viewpoints labeled 1, 2, and 3). For example, the captured image size may be about 2560× 694 pixels, for example. In another embodiment, the image capture devices 440A, 440B, 440C may capture an image size that may be about 1280×387 pixels, for example. Other image sizes and pixel densities may be used.

Each of the image capture devices 440A, 440B, 440C may be configured and operable to capture lateral images of at least a portion of the specimen container 102, and at least a portion of the specimen 212. For example, the image capture devices 440A-440O may capture a part of the label 218 and part or all of the serum or plasma portion 212SP. For example, in some instances, part of a viewpoint 1-3 may be partially occluded by label 218. In some embodiments, one or more of the viewpoints 1-3 may be fully occluded, i.e., no clear view of the serum or plasma portion 212SP is possible. However, even in cases where a side (front side or back side) of a viewpoint 1-3 is fully occluded by one or more labels 218, the characterization method may still be able to distinguish the boundaries of the serum or plasma portion 212SP through the one or more occluding labels 218.

In the embodiment shown, the plurality of image capture devices 440A, 440B, 440C are configured to capture lateral images of the specimen container 102 and specimen 212 at an imaging location 432 from the multiple viewpoints 1-3. The viewpoints 1-3 may be spaced so that they are approximately equally spaced from one another, such as about 120° from one another, as shown. As depicted, the image capture devices 440A, 440B, 440C may be arranged around the track 121. Other arrangements of the plurality of image capture devices 440A, 440B, 440C may be used. In this way, the images of the specimen 212 in the specimen container 102 may be taken while the specimen container 102 is residing in the carrier 122 at the imaging location 432. The field of view of the multiple images obtained by the image capture devices 440A, 440B, 440C may overlap slightly in a circumferential extent.

In one or more embodiments, the carriers 122 may be stopped at a pre-determined location in the quality check module 130, such as at the imaging location 432, i.e., such as at a point where normal vectors from each of the image capture devices 440A, 440B, 440C intersect each other. A gate or the linear motor of the carrier 122 may be provided to stop the carriers 122 at the imaging location 432, so that multiple quality images may be captured thereat. In an embodiment where there is a gate at the quality check module 130, one or more sensors (like sensors 116) may be used to determine the presence of a carrier 122 at the quality check module 130.

The image capture devices 440A, 440B, 440C may be provided in close proximity to and trained or focused to capture an image window at the imaging location 432, wherein the image window is an area including an expected location of the specimen container 102. Thus, the specimen container 102 may be stopped so that it is approximately located in a center of the view window in some embodiments. Within the images captured, one or more reference datum may be present.

In operation of the quality check module 130, each image may be triggered and captured responsive to a triggering signal provided in communication lines 443A, 443B, 443C that may be sent by the computer 143. Each of the captured images may be processed by the computer 143 according to one or more embodiments. In one particularly effective method, high data rate (HDR) processing may be used to capture and process the image data from the captured images. In more detail, multiple images are captured of the specimen 212 at the quality check module 130 at multiple different exposures (e.g., at different exposure times) while being sequentially illuminated at one or more different spectra. For example, each image capture device 440A, 440B, 440C may take 4-8 images of the specimen container 102 including the serum or plasma portion 212SP at different exposure times at each of multiple spectra. For example, 4-8 images may be taken by image capture device 440A at viewpoint 1 while the specimen 212 is backlit illuminated with light source 444A that has a red spectrum. Additional like images may be taken sequentially at viewpoints 2 and 3.

In some embodiments, the multiple spectral images may be accomplished using different light sources 444A-444C emitting different spectral illumination. The light sources 444A-444C may back light the specimen container 102 (as shown). A light diffuser may be used in conjunction with the light sources 444A-444C in some embodiments. The multiple different spectra light sources 444A-444C may be RGB light sources, such as LEDs emitting nominal wavelengths of 634 nm+/−35 nm (Red), 537 nm+/−35 nm (Green), and 455 nm+/−35 nm (Blue). In other embodiments, the light sources 444A-444C may be white light sources. In cases where the label 218 obscures multiple viewpoints, IR backlighting or NIR backlighting may be used. Furthermore, RGB light sources may be used in some instances even when label occlusion is present. In other embodiments, the light sources 444A-444C may emit one or more spectra having a nominal wavelength between about 700 nm and about 1200 nm.

In the way of a non-limiting example, to capture images at a first wavelength, three red light sources 444A-444C (wavelength of about 634 nm+/−35 nm) may be used to sequentially illuminate the specimen 212 from three lateral locations. The red illumination by the light sources 444A-444C may occur as the multiple images (e.g., 4-8 images or more) at different exposure times are captured by each image capture device 440A-440C from each viewpoint 1-3. In some embodiments, the exposure times may be between about 0.1 ms and 256 ms. Other exposure times may be used. In some embodiments, each of the respective images for each image capture device 440A-440O may be taken sequentially, for example. Thus, for each viewpoint 1-3, a group of images are sequentially obtained that have red spectral backlit illumination and multiple (e.g., 4-8 exposures, such as different exposure times). The images may be taken in a round robin fashion, for example, where all images from viewpoint 1 are taken followed sequentially by viewpoints 2 and 3.

In each embodiment, the quality check module 130 may include a housing 446 that may at least partially surround or cover the track 121 to minimize outside lighting influences. The specimen container 102 may be located inside the housing 446 during the image-taking sequences. Housing 446 may include one or more doors 446D to allow the carriers 122 to enter into and/or exit from the housing 446. In some embodiments, the ceiling may include an opening 446O to allow a specimen container 102 to be loaded into the carrier 122 by a robot including moveable robot fingers from above.

Once the red illuminated images are captured in the embodiment of FIGS. 4A-4B, another spectra of light, for example, green spectral light sources 444A-444C may be turned on (nominal wavelength of about 537 nm with a bandwidth of about +/−35 nm), and multiple images (e.g., 4-8 or more images) at different exposure times may be sequentially captured by each image capture device 440A, 440B, 440C. This may be repeated with blue spectral light sources 444A-444C (nominal wavelength of about 455 nm with a bandwidth of about +/−35 nm) for each image capture devices 440A, 440B, 440C. The different nominal wavelength spectral light sources 444A-444C may be accomplished by light panels including banks of different desired spectral light sources (e.g., R, G, B, W, IR, and/or NIR) that can be selectively turned on and off, for example. Other means for backlighting may be used.

The multiple images taken at multiple exposures (e.g., exposure times) for each respective wavelength spectra may be obtained in rapid succession, such that the entire collection of backlit images for the specimen container 102 and specimen 212 from multiple viewpoints 1-3 may be obtained in less than a few seconds, for example. In one example, 4 different exposure images for each wavelength at three viewpoints 1-3 using the image capture devices 440A, 440B, 440C and back lighting with RGB light sources 444A-444C will result in 4 images×3 spectra×3 image capture devices=36 images. In another example, 4 different exposure images for each wavelength at three viewpoints using the image capture devices 440A, 440B, 440C and back lighting with R, G, B, W, IR, and NIR light sources 444A-444C will result in 4 images×6 spectra×3 cameras=72 images.

According to embodiments of the characterization methods, the processing of the image data may involve a pre-processing step including, for example, selection of optimally-exposed pixels from the multiple captured images at the different exposure times at each wavelength spectrum and for each image capture device 440A-440O, so as to generate optimally-exposed image data for each spectrum and for each viewpoint 1-3. This is referred to as "image consolidation" herein.

For each corresponding pixel (or patch), for each of the images from each image capture device 440A-440O, pixels (or patches) exhibiting optimal image intensity may be selected from each of the different exposure images for each viewpoint 1-3. In one embodiment, optimal image intensity may be pixels (or patches) that fall within a predetermined range of intensities (e.g., between 180-254 on a scale of 0-255), for example. In another embodiment, optimal image intensity may be between 16-254 on a scale of 0-255), for example. If more than one pixel (or patch) in the corresponding pixel (or patch) locations of two exposure images is determined to be optimally exposed, the higher of the two is selected.

The selected pixels (or patches) exhibiting optimal image intensity may be normalized by their respective exposure times. The result is a plurality of normalized and consolidated spectral image data sets for the illumination spectra (e.g., R, G, B, white light, IR, and/or IR—depending on the combination used) and for each image capture device 440A-440O where all of the pixels (or patches) are optimally exposed (e.g., one image data set per spectrum) and normalized. In other words, for each viewpoint 1-3, the data pre-processing carried out by the computer 143 results in a plurality of optimally-exposed and normalized image data sets, one for each illumination spectra employed.

Figure 5A:
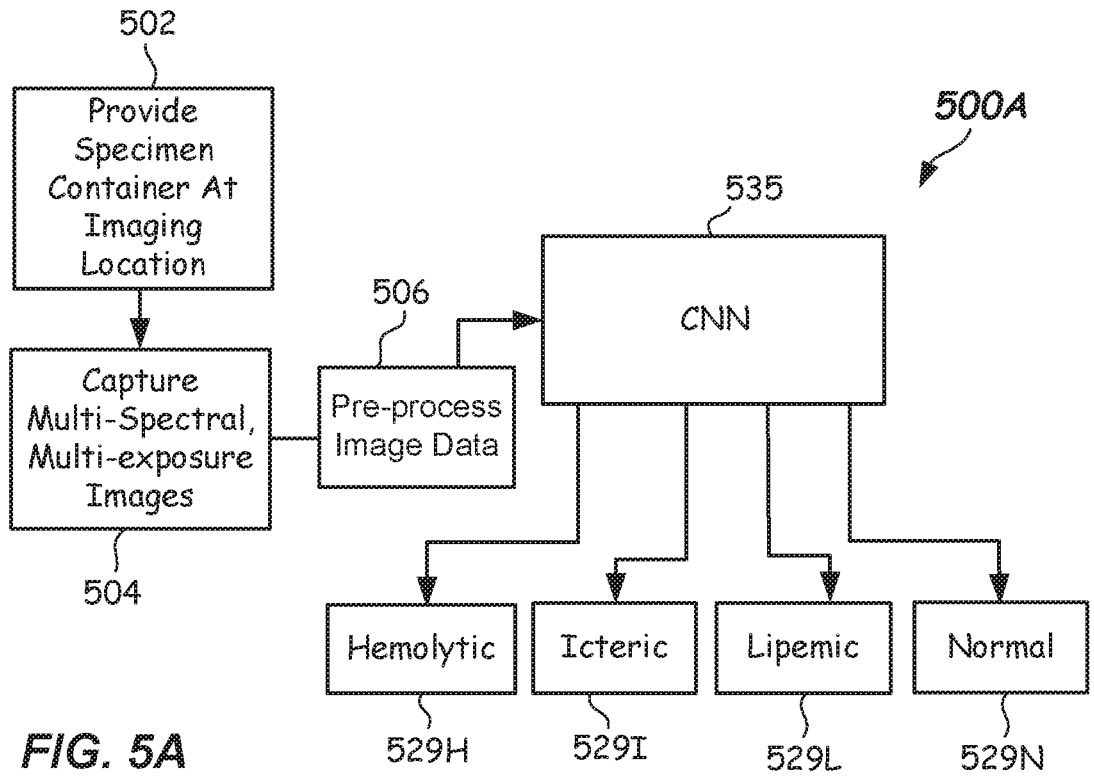
FIG. 5A illustrates a block diagram of functional components of a quality check module including a CNN configured to determine a presence of H, I, and/or L or N in a specimen according to one or more embodiments.

Functional components of one embodiment of apparatus 500A configured to carry out the HILN characterization method are shown in FIG. 5A. The apparatus 500A may be embodied as a quality check module 130. As discussed above, the specimen container 102 is provided at the imaging location 432 (FIGS. 4A-4B) of the quality check module 130 in 502. The multi-spectral, multi-exposure images are captured in 504 by the one or more image capture devices 440A-440O. The image data for each of the multi-spectral, multi-exposure images may be pre-processed in 506 as discussed above to provide a plurality of optimally-exposed and normalized image data sets (hereinafter "image data sets"). These image data sets may be supplied as layers (as matrices) as input to the CNN 535, which has been previously trained to recognize HILN.

Multiple sets of training examples are used to train the CNN 535. The CNN 535 is trained in CNN training by imaging with the quality check module 130 a multitude of samples of specimen containers 102 containing specimen 212 by graphically outlining various regions of a multitude of examples of specimens 212 having various specimen HILN conditions, outlining the various regions of occlusion by label 218, levels of serum or plasma portion 212SP, and the like. Along with the graphical outlines, class characterization information for each area is provided. As many as 500 or more, 1000 or more, 2,000 or more, or even 5,000 or more images may be used for training the CNN 535. Each training image may have at least the serum or plasma portion 212SP, its H, I, L, or N identified, various index levels (if output), and the label 218 outlined manually to identify and teach the CNN 535 the areas that belong to each class that will be a possible output. The CNN 535 may be tested intermittently with a sample specimen container to see if the CNN 535 is operating at a sufficiently high level of confidence. If not operating at 100% (e.g., 98% confidence level or more) in determining the correct HILN configuration as an output, then more training samples may be imaged and input along with associated characterization information. In embodiments where segmentation is also provided, the training involves outlining the segmented classes outputted and including as input class identification information.

In the present embodiment of FIG. 5A, the outputs from the CNN 535 are one of hemolytic (H) at 529H, Icteric (1) at 529I, lipemic (L) at 529L, and normal (N) at 529N. Each (pixel or patch) that is processed by the CNN 535 has an output to one of HILN. These per pixel (or per patch) results may be summed and HILN determined based on which of the HILN has the highest count. In some embodiments, when the processing on all pixels (or patches) identified as serum or plasma portion 212SP is completed, there may be pixels (or patches) that have substantial votes for more than one of HILN. For example, there may be large number of counts for H and also a large number of counts for L.

In order to estimate the final vote for HILN, post processing may be provided to traverse all serum pixels (or patches) from each viewpoint and create a histogram over all the occurrences (counts). The histogram may be normalized to 1.00. Thus, there may be more than one class output (e.g., H and L) that are lower than 1.00, depending on how many pixels (or patches) have a vote for the particular class. Thus, the output may be a primary class and a secondary class in some embodiments, based on the number of normalized votes obtained for each.

Figure 5B:
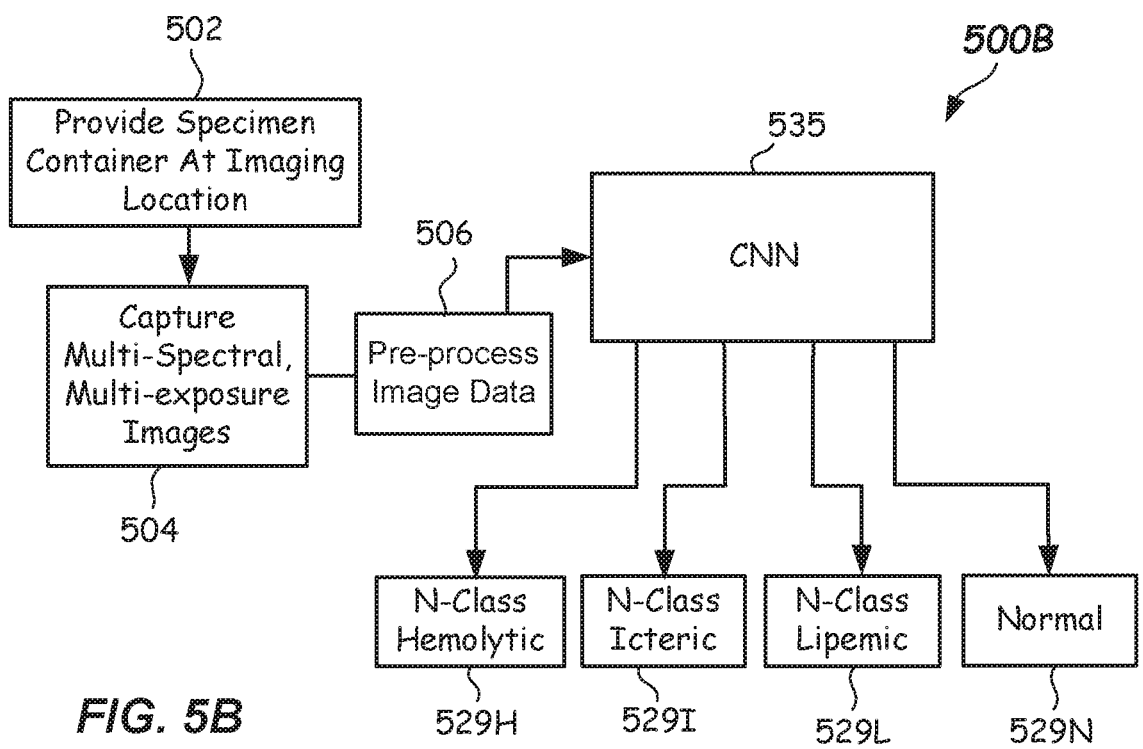
FIG. 5B illustrates a block diagram of functional components of another quality check module including a CNN configured to determine a presence of N-Class Hemolytic, N-Class Icteric, and/or N-Class Lipemic, or N according to one or more embodiments.

Referring now to FIG. 5B, another embodiment of apparatus 500B is shown, wherein the output of the CNN 535 may be N-class hemolytic 529H, N-class icteric 529I, N-class lipemic 529L, or normal (N) 529N, wherein N-class is the number (N) of class options in that interferent class. As before, multi-spectral, multi-exposure consolidated and normalized image data sets are input into the CNN 535 and the image data sets are operated upon and processed by the CNN 535. The output of the processing with the CNN in 535 may be multiple output possibilities (N-classes) for each of HIL, and of course for each viewpoint.

Figure 5C:
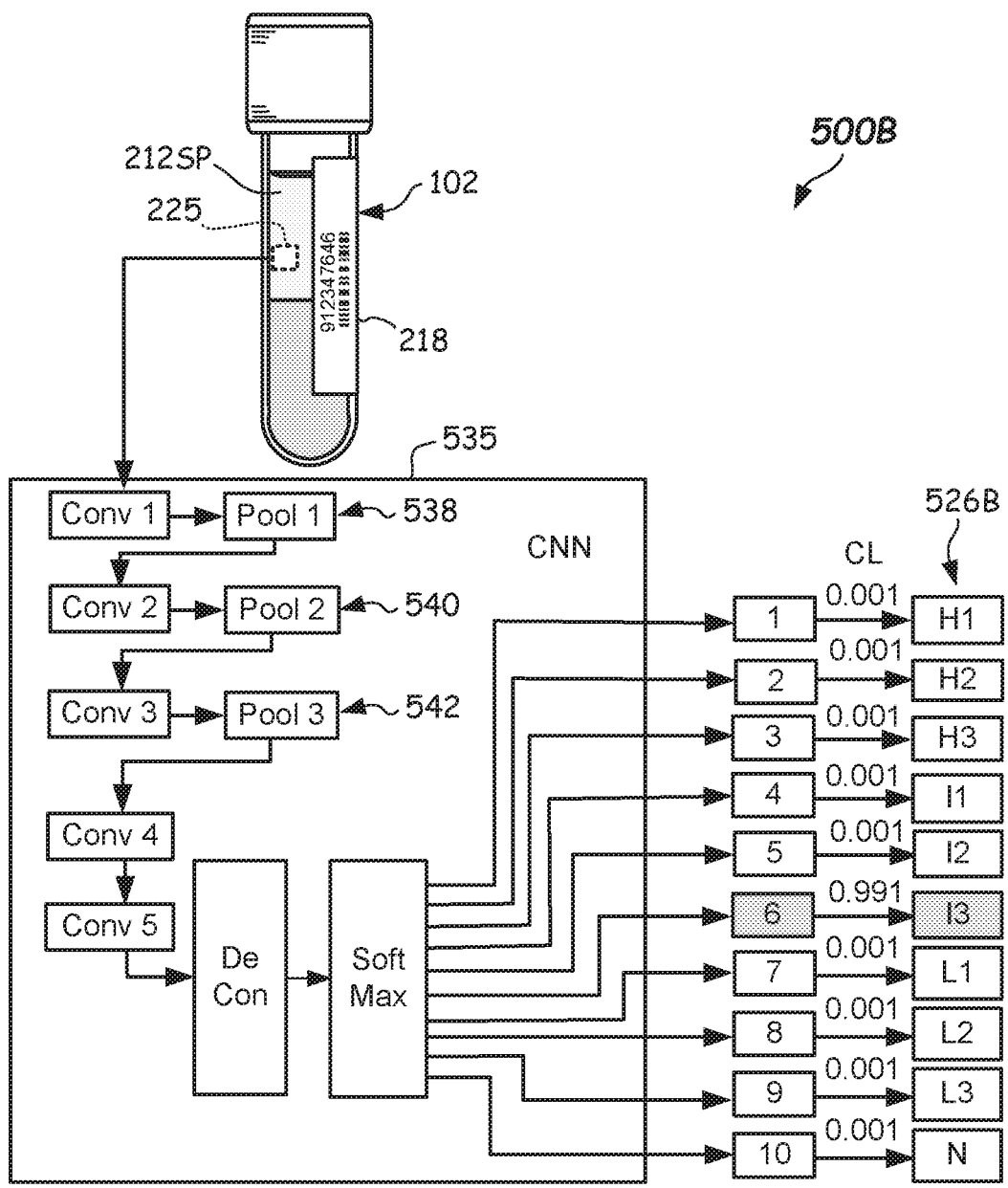
FIG. 5C illustrates a block diagram of functional components of another quality check module showing one architecture of a CNN configured to determine a presence of H1, H2, H3, I1, I2, I3, L1, L2, L3, or N according to one or more embodiments.

For example, as is shown in the apparatus 500B of FIG. 5C, which represent one possible CNN architecture, the output of the CNN may be N-Classes (n=3) of HIL and per-channel confidence levels (CL) for HILN, wherein each channel 1-10 is correlated with a particular class type (e.g., H1, H2, H3, I1, I2, I3, L1, L2, L3, and N) at 526B. Thus, for each pixel (or patch), an outputted class (H1-N) is provided. These per pixel (or per patch) outputs may be aggregated by any suitable post processing routine to sum up or otherwise process the results of each channel and arrive at an overall determination of HILN from the available classes (e.g., H1, H2, H3, I1, I2, I3, L1, L2, L3, and N). Any suitable voting scheme may be used, such as final pixel class=max CL, and then adding up the number of max CL for the serum or plasma portion 212SP. This same processing may be achieved per viewpoint. The per pixel (or per patch) classification results or overall results of the viewpoints may be summed or otherwise consolidated or averaged. Although three possible levels of H, I and L are shown, it should be recognized that more or less output options may be possible (e.g., 2, 4, 5, or more).

Based upon the output of the CNN 535 for any particular specimen container 102 and specimen 212 being pre-screened, one or more further actions may be implemented. For example, if the pre-screening for H, I, or L level is too high (e.g., above a threshold), then the specimen 212 may be rejected, subject to further processing, subject to retest, and/or may be offloaded from the quality control module 130 or specimen testing apparatus 100. Notice of the pre-screening HILN results from the CNN 535 may be provided to the operator of the specimen testing apparatus 100 and/or to the LIS 147.

One example architecture of the CNN 535 is shown in FIG. 5C. This CNN 535 and the other CNNs described herein may be coded using any suitable scientific computing framework, program, or toolbox, such as, for example, Caffe available from Berkley Vision and Learning Center (BVLC), Theano, a Python framework for fast computation of mathematical expressions, TensorFlow, Torch, and the like.

In more detail, the CNN 535 may include suitable number of operating layers to provide for deep learning. For example, the CNN may comprise an architecture including at least two layers including convolution and pooling, and at least two additional fully-convolution layers. In the present embodiment, three operating layers 538, 540, 542 are provided, and well as two fully-convolutional layers. The described CNN architecture may be used for classification of an input patch 225 from each layer of image data that may scanned with a moving window approach. The moving window of input patch 225 may be a 64×64 patch (64×64 pixels), for example. However, other sizes of patches may be used. Three major operating layers are shown, for example. The first layer 538 may extract very local structure edges; the second layer 540 learns texture, which is a combination of edges; and the third layer 542 forms the parts. Each of the layers 538, 540, 542 of the CNN 535 benefit from the multichannel input (e.g., multi-spectral, multi exposure information) which is processed. These operations over various input layers, and in particular three input layers (e.g., RGB), can be easily handled and represented by the deep learning network. This framework naturally integrates low, mid, and high level features, and leads to multilayer classification. In one or more embodiments, the image data may exclude bar code regions from the classification since they may introduce artefacts due to signal blocking.

During data preparation, small patches may be extracted that fulfil defined criteria. For example, the criteria may include serum or plasma portions 212SP and only regions of labels 218 with low variance, such as white regions with no barcode elements and/or fonts. The training may first utilize an erosion operation to the defined regions by a 16×16 element. A moving window of input patch 225 (e.g., size 64×64 pixels) with step of 1 pixel may be used to scan through the eroded regions. If some resulting patch centers at a pixel that belongs to the eroded region, it will be considered. Sampling using patches from the training images create the representation required for deep learning. The features are stored in a database and used for later testing. Training the CNN 535 may involve an N-class classification task with input on each of the possible class outcomes (H1-N) at 526B. Training may continue including providing as input (annotating) graphical outlining of the serum or plasma portion 212SP and label 218 and providing class information until suitable confidence in the CNN 535 is achieved.

Again referring to FIG. 5C, the CNN 535 includes a first layer 538 including a convolution layer (Conv 1), which may include 10 filters of size 5×5×12, for example. Other numbers of filters and filter sizes may be used. The resulting 10 feature maps are then fed to a max-pooling (Pool 1), which may take the max over 2×2 spatial neighborhoods with a stride of 1, separately for each channel. The purpose of this layer is to extract low-level features, especially like simple edges. This is followed by a the second layer 540 including a convolution layer (Conv 2) that may have 10 filters of size 5×5×20, and a max-pooling layer (Pool 2) which may take the max over 3×3 spatial neighborhoods with a stride of 2. The purpose of the second layer 540 is to learn different combination of simple edges to form texture. Thereafter, the resulting feature maps are fed into a third layer 542 including a convolution layer (Conv 3) that may have 20 filters of size 3×3×20, and a max-pooling layer (Pool 3), which may take the max over 2×2 spatial neighborhoods with a stride of 2 to learn combination of textures to form parts. Aforementioned max-pooling layers make the output of convolution networks more robust to local translations. Finally, the top layers (Conv 4 and Conv 5) are fully convolutional layers wherein each output unit is connected to all inputs. These layers are able to capture correlations between parts. The output of the last convolutional layer (Conv 5) is fed to de-convolutional layer (De-Con) and then a n-way SoftMax (where n=10 is the number of possible output classes) which produces a distribution over the n-class output channels. In short, the moving window of input patch 225, where each patch is classified with the trained CNN 535, gives a response towards one of the n-classes. Classification for the corresponding image data sets may be the majority voting results from these outputs. An additional step may be applied where per viewpoint results may be aggregated over the multiple viewpoints to obtain a confident decision, such as by averaging the results of the multiple viewpoints.

Figure 5D:
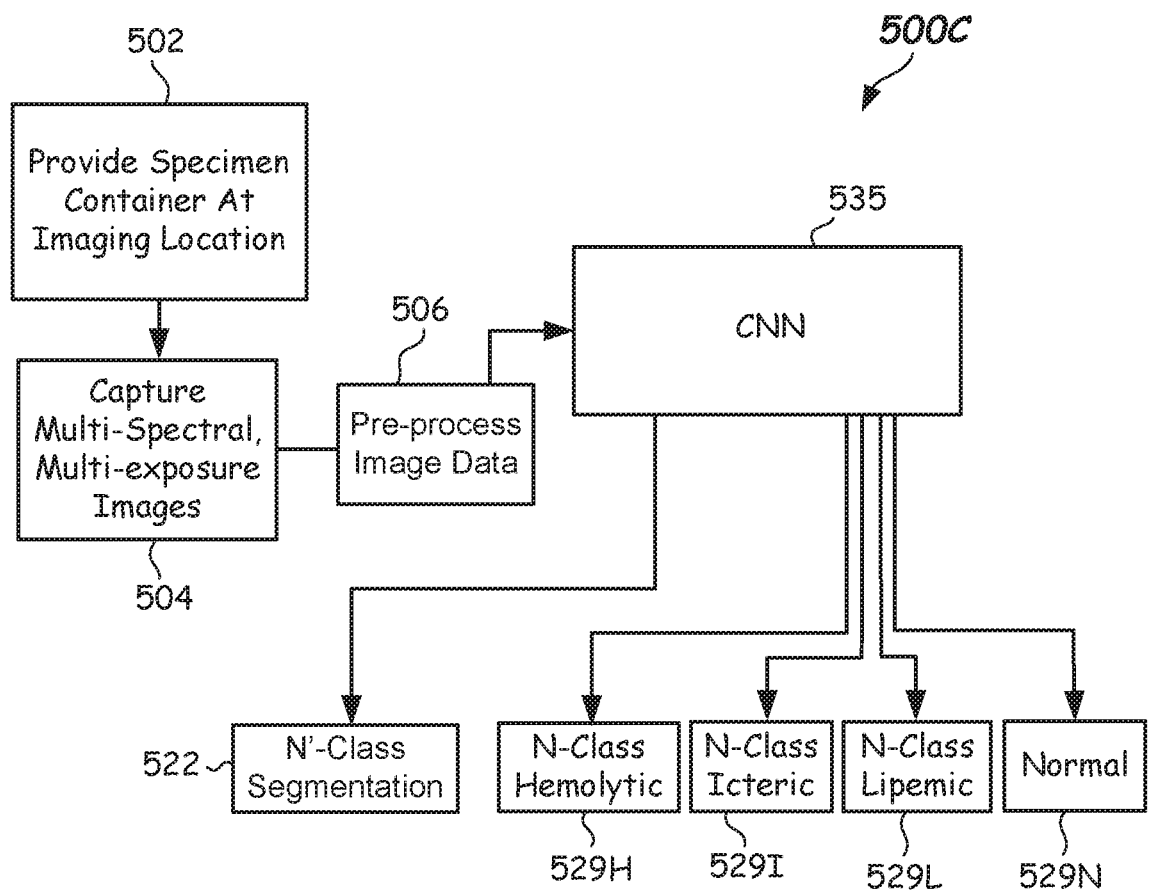
FIG. 5D illustrates a block diagram of functional components of another quality check module including a CNN configured to determine a presence of N'-Class Segmentation together with N-Class Hemolytic, N-Class Icteric, and/or N-Class Lipemic, or N according to one or more embodiments.
Figure 5E:
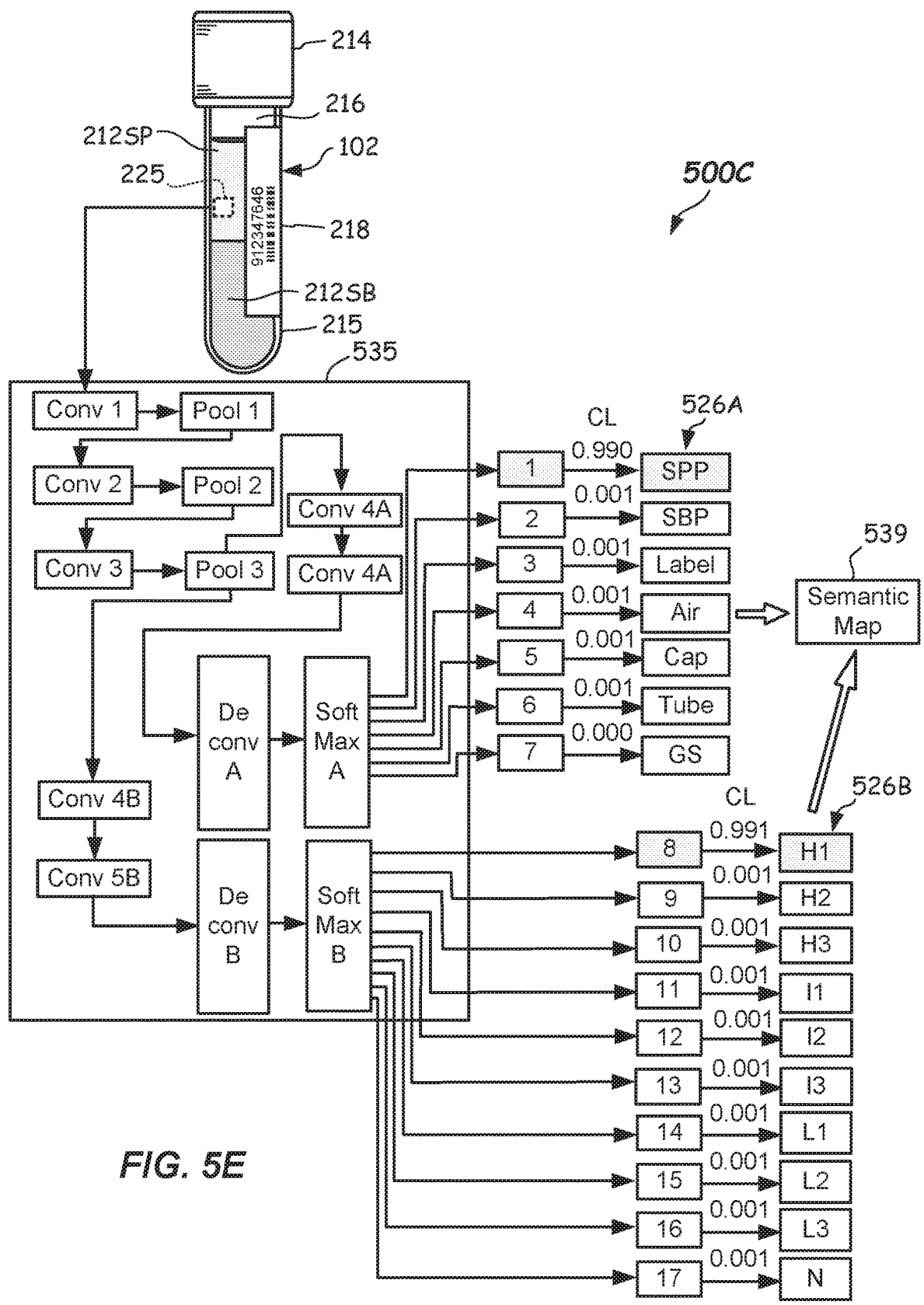
FIG. 5E illustrates a block diagram of functional components of a quality check module showing an architecture of a CNN configured to include two branches, a first branch to determine a N'-Class segmentation, and a second branch to determine N-Class HILN according to one or more embodiments.

FIGS. 5D and 5E illustrate another embodiment of apparatus 500C showing the functional components configured to carry out the characterization method, wherein the apparatus 500C provides HILN detection and also segmentation as an output from the CNN 535. The apparatus 500C described herein is as previously described in the FIG. 5B-5C embodiment, except that the CNN 535 in this embodiment includes two branches. The first branch provides N'-Class segmentation in 522, wherein N' is the number of segmentation class output options at 526A. For example, the N'-class segmentation may result in segmentation output data of two or more of 1—Serum or Plasma portion (SPP), 2—Settled Blood Portion (SBP), 3—Label, 4—Air, 5—Cap, 6—Tube, 7—Gel Separator (GS), for example. Other segmentations output options may include background and/or holder. The per pixel (or per patch) output to channels 1-7 may provide semantic data regarding classification versus pixel (or patch) location. Such semantic data can be aggregated and may be mapped to provide semantic map 539. Semantic maps 539 may be per viewpoint, or otherwise aggregated to provide a 3D semantic map.

The second branch may provide output classification of N-Class Hemolytic 529H, N-Class Icteric 529I, and/or N-Class Lipemic 529L, or Normal (N) 529N as previously described. Channels 8-17 provide multiple class options (H1-N) as outputs from the CNN 535. The output data of HILN may also be provided as part of the semantic map 539 per viewpoint or as a 3D semantic with a HILN map. The semantic map 539 may be stored in a database in the computer 143. The semantic map 539 can be graphically displayed, and may be color coded for HILN, in some embodiments.

The architecture of the CNN 535 may be as previously described, except that each branch includes fully-convolutional layers Conv 4A, Conv 5A, Conv 4B, Conv 5B, and separate deconvolution layers (Deconv A, Deconv B), and Softmax layers (SoftMax A, SoftMax B).

Because the backlight from the light sources 444A-444C onto the back side of the specimen container 102 in each viewpoint 1-3 may be blocked by the presence of the label 218 that are located on the back side, the intensities of the front view images captured by the image capture devices 440A-440C in front view regions corresponding to the back view regions containing the label 218 may be affected. As such, the intensities in those regions may be suspect and the CNN can appropriately adjust and compensate for this such that the output from the CNN from these occluded regions is adjusted and made equal to the other un-occluded regions of the serum or plasma portion 212SP. Therefore, according to one or more embodiments of the disclosure, the characterization method takes into account label occlusion from the back side.

Figure 5F:
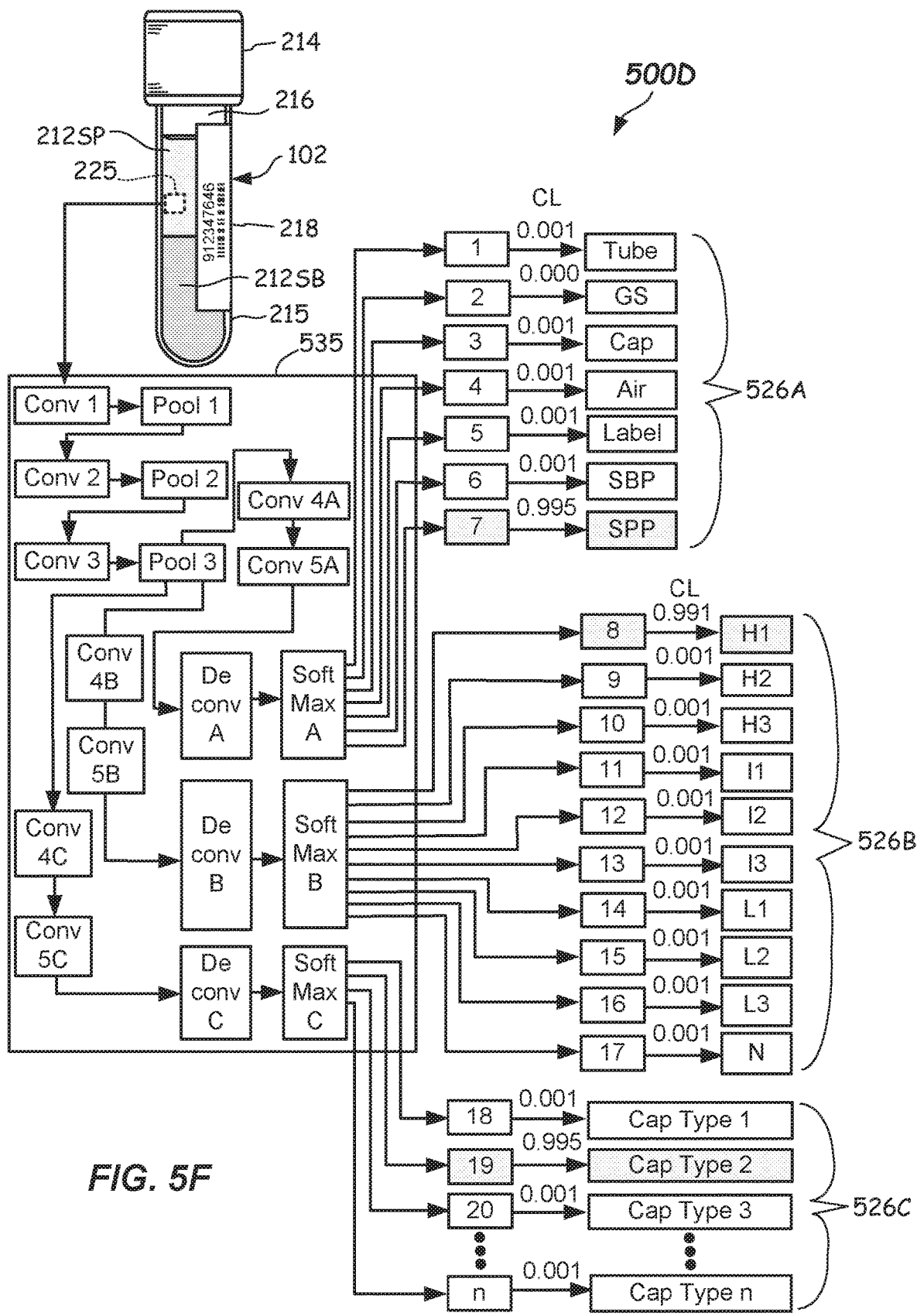
FIG. 5F illustrates a block diagram of functional components of another quality check module showing an architecture of a three-branch CNN architecture configured to determine a N'-class segmentation, N-class HILN, and an n-class cap type according to one or more embodiments.

FIG. 5F illustrates another embodiment of CNN 535 including three branches including classification options 526A-526C. The first and second branches may be the same as described above, whereas the third branch is configured to classify the cap type 526C. Any number of n-classes of cap type may be output from the third branch of the CNN 535. For example, the cap type output options may constitute different colors and/or cap shapes that have previously trained into the CNN 535 by input of graphically outlined cap regions and corresponding cap information and colors. This outcome at 526C may be used as a check as against the ordered tests from the LIS 147 do make sure that an appropriate specimen container 102 was used for the tests that were ordered. The architecture of the CNN 535 may be as previously described, and wherein the third branch includes separate fully-convolutional layers Conv 4C, Conv 5C, deconvolution layer (Deconv C), and Softmax layer (SoftMax C). In some embodiments of the CNN 535, the fully convolutional layers Conv 4, Conv 5 described above may be substituted with fully connected layers. As before, a semantic map may be generated based upon the output results from the CNN 535 of segmentation 526A, HILN 526B, and cap type detection 526C.

Figure 5G:
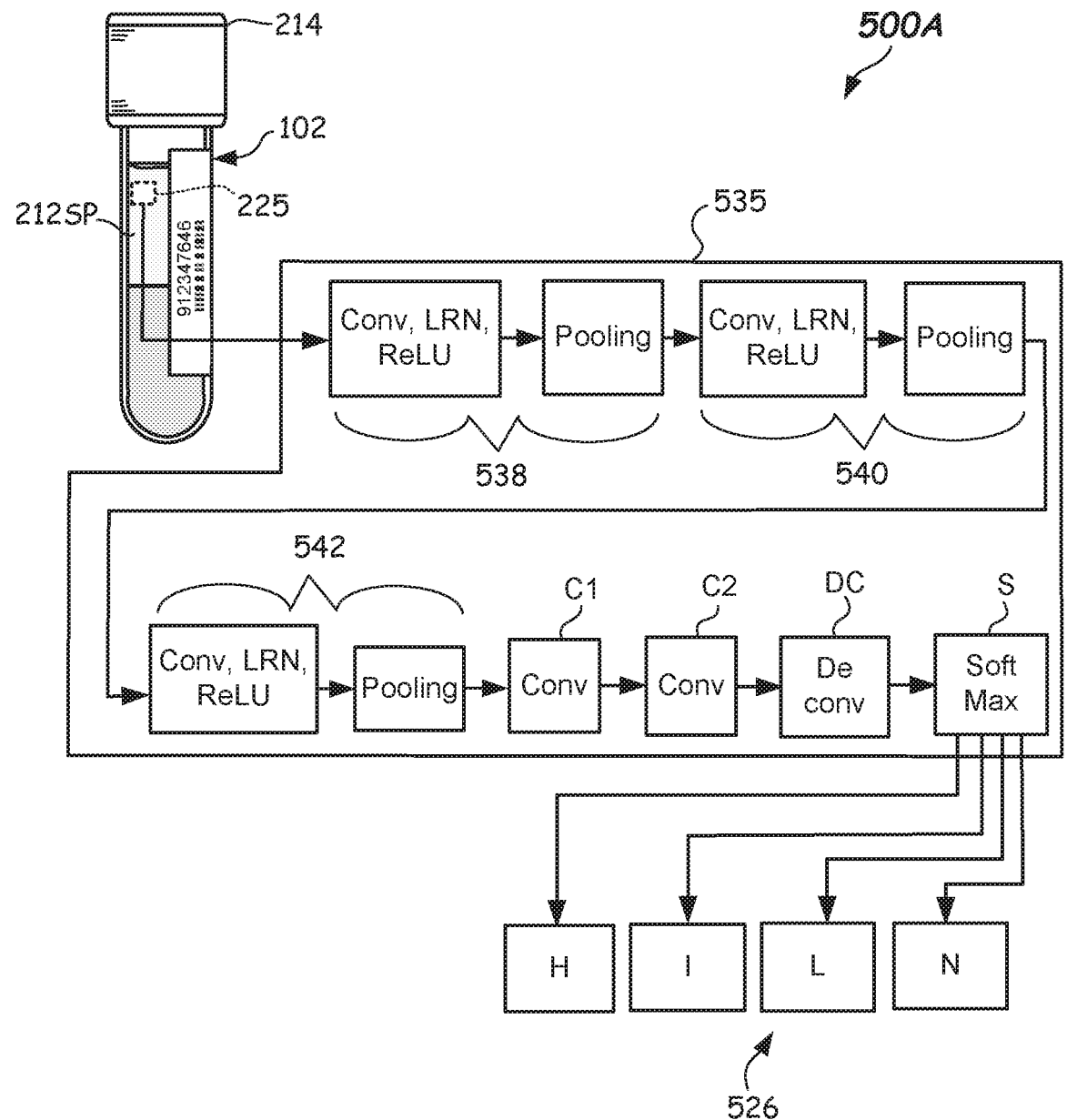
FIG. 5G illustrates a block diagram of functional components of another quality check module including CNN architecture configured to determine a 4-class HILN according to one or more embodiments.

FIG. 5G illustrates another embodiment of apparatus 500A illustrating functional components configured to carry out the characterization method and that includes a different architecture of the CNN 535. This architecture may be used for the apparatus 500A of FIG. 5A, for example. The architecture of the CNN 535 may be as previously described, including fully-convolutional layers C1, C2, deconvolution layer (DC), and Softmax layer (S). However, in this embodiment, the first layer 538, the second layer 540, and the third layer 542 may each include LRN and ReLU features which serve to perform activation functions (ReLU), LRN compensates for disparate value ranges by normalization. The output from the CNN 535 is HILN. Thus, the CNN 535 includes multiple layers including convolution, LRN, and ReLU, fully-convolutional layers, a deconvolution layer, and a SoftMax layer.

Figure 6A:
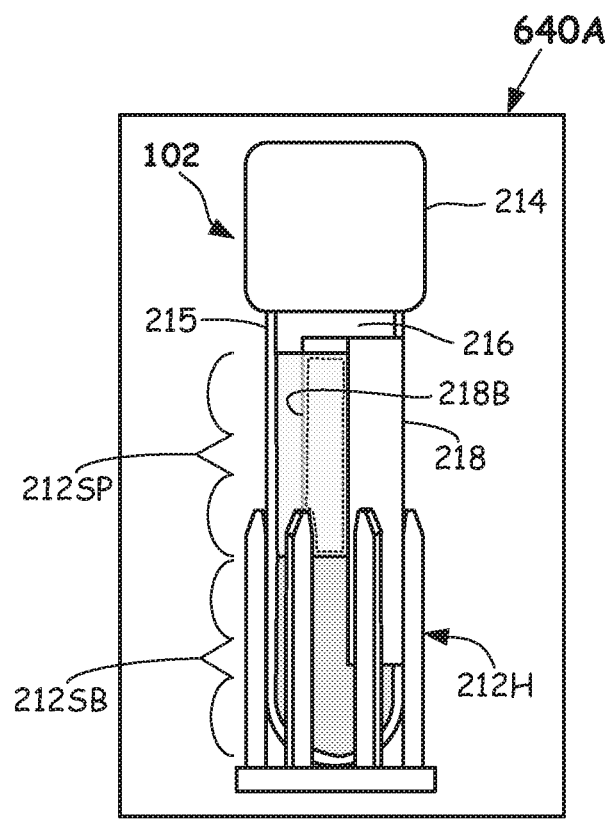
FIG. 6A illustrates a first image from a first viewpoint according to one or more embodiments.
Figure 6B:
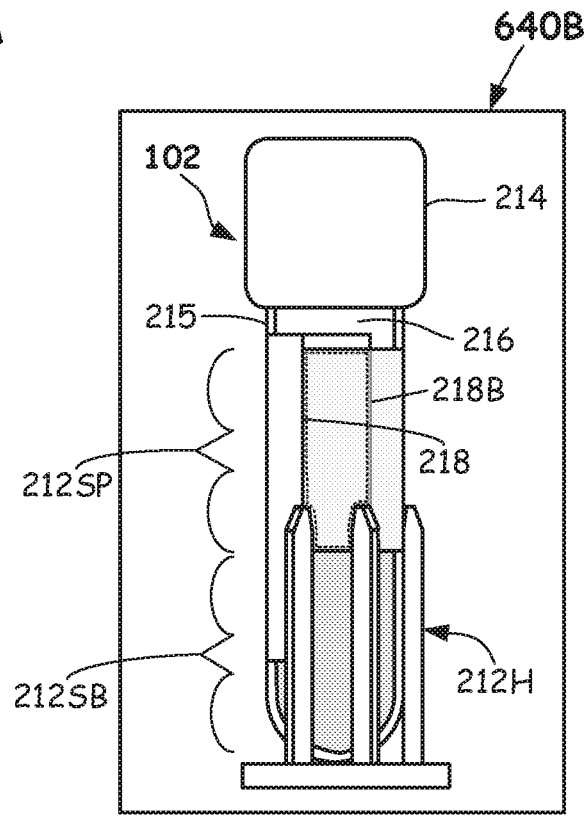
FIG. 6B illustrates a second image from a second viewpoint according to one or more embodiments.
Figure 6C:
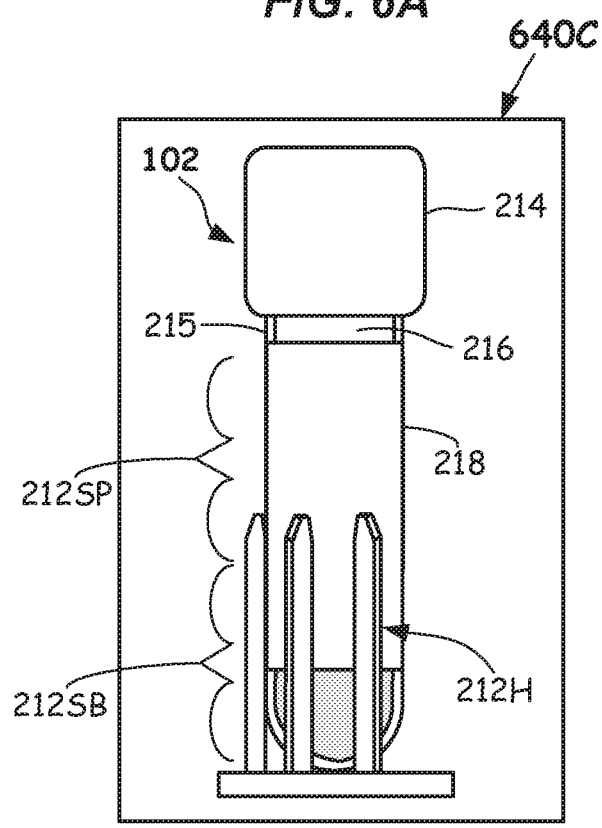
FIG. 6C illustrates a third image from a third viewpoint according to one or more embodiments.
Figure 6D:
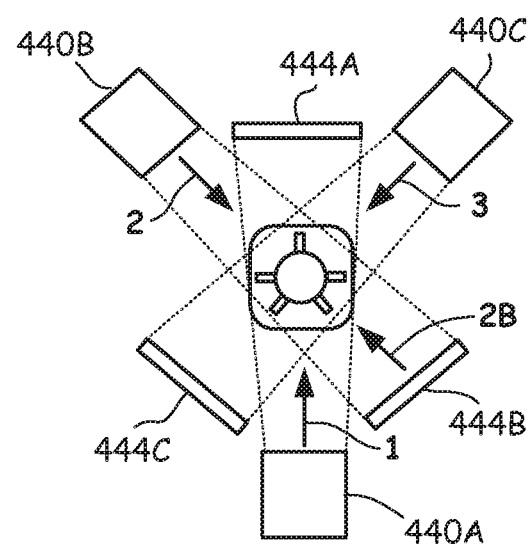
FIG. 6D illustrates a schematic top view illustrating various viewpoints according to one or more embodiments.

FIGS. 6A and 6B illustrate a front semantic image 640A, 640B from a first viewpoint 1, and second viewpoint 2 of image capture devices 440A, 440B (See FIG. 6D). In FIGS. 6A and 6B, some of the serum or plasma portion 212SP is occluded by label 218, and some of the backlight emitted from light sources 444A, 444B (FIG. 6D) is blocked by the back view label 218B (i.e., the portion of the label 218 that is occluded is shown dotted).

FIG. 6C illustrates a front semantic image 640C from viewpoint 3 of image capture device 440C (FIG. 6D). In FIG. 6C, all of the serum or plasma portion 212SP is occluded by label 218 from viewpoint 3. For each of these viewpoints 1, 2, 3, the CNN 535 may output an HILN on a per pixel basis (or per patch basis). Thus, the characterization method may aggregate the results for each viewpoint 1, 2, 3 and provide an overall determination of HILN for each viewpoint. In each case, the trained CNN 535 takes into the serum or plasma portion 212SP that is visible but also the regions occluded by the back view label 218B. The results from each view may be aggregated or averaged to arrive at an overall reading. For example, in some embodiments, the HILN results from viewpoints 1 and 2 may be included. The results of viewpoint, because it is fully occluded may be ignored, or if a suitable HILN measure can be obtained, then it may also be averaged to arrive at an overall HILN reading for the serum or plasma portion 212SP. In other embodiments, the best view only may be reported, which may be the viewpoint having the most un-occluded view.

Thus, in one embodiment, if a majority of pixels (or patches) are classified as N, then the serum or plasma portion 212SP may be categorized as normal (N). If a majority of pixels (or patches) are classified as H, then the serum or plasma portion 212SP may be categorized as containing hemolysis (H). Likewise, if a majority of pixels (or patches) are classified as I or L, then the serum or plasma portion 212SP may be categorized as Icterus (I), or lipemia (L), respectively. In other embodiments, a weighted majority voting scheme may be also used to classify the specimen 212 using probabilities from the HILN results as a weight. Other means for characterizing the serum or plasma portion 212SP, as a whole, may be used. Moreover, if the output data set contains a relatively large amount of pixels (or patches) that are classified in two or more interferent classes (e.g., H and I, H and L, I and L, or even H, I, and L), then the interferent detection method may report that multiple interferent types are present.

Figure 7:
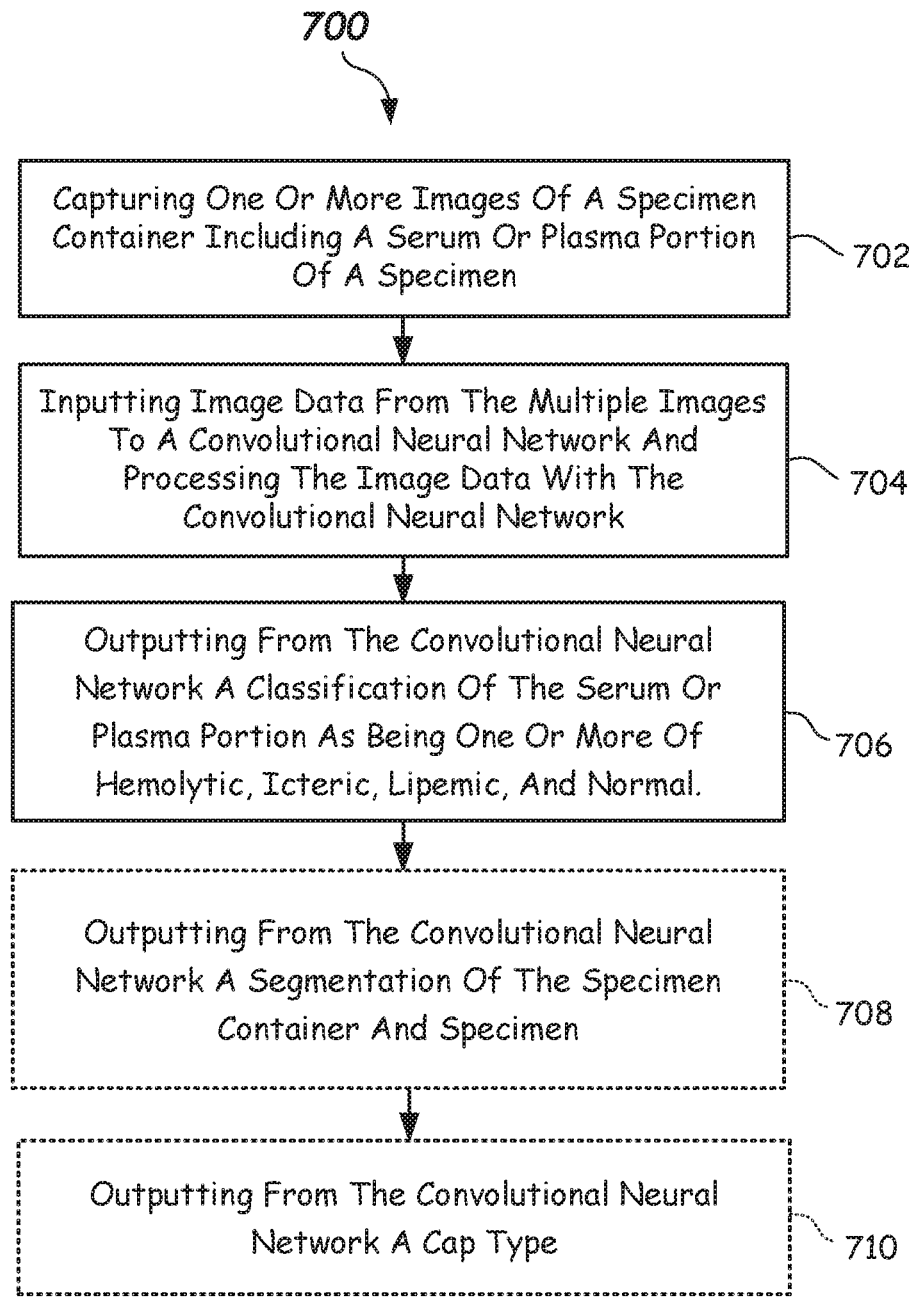
FIG. 7 is flowchart of a method of determining H, I, and/or L, or N in a specimen according to one or more embodiments.

FIG. 7 illustrates a flowchart of a characterization method 700 according to embodiments of the disclosure. The characterization method 700 may be carried out by quality check module 130 as described herein. In particular, the characterization method 700 may determine a presence of an interferent in a specimen 212 according to one or more embodiments. The characterization method 700 includes, in 702, capturing multiple images of a specimen container (e.g., specimen container 102) including a serum or plasma portion (e.g., serum or plasma portion 212SP) of a specimen (e.g., specimen 212). The capturing multiple images may be from multiple viewpoints (e.g., viewpoints 1, 2, and 3). Moreover, the specimen container 102 may include one or more labels (e.g., label 218) thereon. The one or more images may be digital, pixelated images captured using one or more image capture devices (e.g., image capture devices 440A-440C).

The characterization method 700 further includes, in 704, inputting image data (e.g., consolidated and normalized image data sets) from the multiple images to a convolutional neural network (e.g., CNN 535) and processing the image data with the convolutional neural network. The processing may be accomplished by the computer 143 described herein after suitable training of the CNN 535.

The characterization method 700 further includes, in 706, outputting from the convolutional neural network (e.g., CNN 535) a classification of the serum or plasma portion as being one or more of hemolytic, icteric, lipemic, and normal (i.e., H, I, L, H and I, H and L, I and L, H, I, and L, or N).

The multiple images may include multiple images at each viewpoint at different exposure times and/or at different spectral illumination (e.g., R, G, B, white light, IR, and/or near IR). For example, there may be 4-8 different exposures or more taken at different exposure times for each viewpoint under the different spectral illumination conditions.

In an optional aspect, in addition to the HILN determination, a segmentation of the image data sets may be obtained. The method 700 may, in 708, output from the convolutional neural network (e.g. CNN 535 of FIG. 5D-5F) a segmentation of the specimen container 102 and specimen 212. The image data may be segmented into N'-classes (e.g., 7 classes), such as 1—Tube, 2, gel separator, 3—Cap, 4—Air, 5—Label, 6—settled blood portion, and/or 7—serum or plasma portion. Other numbers of classes may be used.

The characterization method 700 may optionally include, in 710, outputting from the convolutional neural network (e.g., CNN 535 of FIG. 5F) a cap type, which may be a specific cap shape or cap color that was pre-trained into the CNN 535.

Accordingly, based on the foregoing it should be apparent that an improved characterization method 700 is provided that better characterizes the serum or plasma portion 212SP by accounting for labels that may occlude the one or more viewpoints. The improved characterization may be used to provide a rapid and robust characterization of a presence of HILN of the specimen 212 (FIGS. 5A-5G), and in some embodiments, an interferent level (H1, H2, H3, I1, I2, I3, L1, L2, L3) may be assessed and output from the CNN 535 (See FIGS. 5C-5F).

As should be apparent, the above characterization methods may be carried out using a quality check module (e.g., quality check module 130), comprising a plurality of image capture devices (e.g., image capture devices) 440A-440C arranged around an imaging location (e.g., imaging location 432), and configured to capture multiple images from multiple viewpoints (e.g., multiple viewpoints 1-3) of a specimen container 102 including one or more labels 218 and containing a serum or plasma portion 212SP of a specimen 212, and a computer (e.g., computer 143) coupled to the plurality of image capture devices and adapted to process image data of the multiple images. The computer (e.g., computer 143) may be configured and capable of being operated to process the multiple images from the multiple viewpoints (e.g., viewpoints 1-3) to provide HILN determination or HILN determination in combination with segmentation for each of the multiple viewpoints.

Further, the characterization method 700 may be carried out on a specimen testing apparatus 100 including the quality check module 130. The specimen testing apparatus 100 may include a track 121, and a carrier 122 moveable on the track 121. The carrier 122 may be configured to contain and support the specimen container 102 including the one or more labels 218 and containing a serum or plasma portion 212SP of a specimen 212 and carry the specimen container 102 to the quality check module 130 to accomplish the characterization and the pre-screening for the presence of an interferent.

Various selected components, features, or embodiments may be described individually herein. It should be noted that such components, features, or embodiments may be used in substitution with other individually-described components, features, or embodiments, or even in combination with other described components, features, or embodiments herein, as is practical. While the invention is susceptible to various modifications and alternative forms, specific apparatus, system, and methods have been shown by way of example in the drawings and are described in detail herein. It should be understood, however, that it is not intended to limit the disclosure to the particular apparatus, systems, and methods disclosed but, to the contrary, the intention is to cover all modifications, equivalents, and alternatives falling within the scope of the appended claims.

What is claimed is:

1. A characterization method, comprising:
    capturing multiple images of a specimen container including a serum or plasma portion of a specimen;
    inputting image data from the multiple images to a convolutional neural network and processing the image data with the convolutional neural network; and
    outputting from the convolutional neural network a classification of the serum or plasma portion as being one or more of hemolytic, icteric, lipemic, and normal; wherein:
    the convolutional neural network comprises an architecture including at least two layers including convolution and pooling, and at least two additional fully convolution layers.

2. The method of claim 1, wherein the capturing multiple images comprises capturing multiple images at different exposure times for each of multiple spectra.

3. The method of claim 1, wherein the capturing the multiple images comprise providing different exposure times for each spectrum of red, green, and blue.

4. The method of claim 1, wherein the multiple images are captured from multiple viewpoints and comprise multi-spectral, multi-exposure images for each viewpoint.

5. The method of claim 4, wherein the specimen container includes one or more labels occluding at least part of one viewpoint.

6. The method of claim 1, wherein the convolutional neural network architecture includes at least three layers including the convolution and pooling, and a deconvolutional layer and a SoftMax layer.

7. The method of claim 1, wherein the convolutional neural network comprises:
    multiple layers including convolution, LRN, and ReLU, fully convolutional layers, a deconvolution layer, and a SoftMax layer.

8. The method of claim 1, wherein the classification of the serum or plasma portion comprises output options of N-classes for each of hemolytic, icteric, and lipemic.

9. The method of claim 1, wherein the classification of the serum or plasma portion comprises output options of fine-grained indexes for each of hemolysis, icterus, and lipemia.

10. The method of claim 1, wherein the capturing the multiple images comprises backlighting with light sources comprising one or more spectra of R, G, B, white light, infrared (IR), and near IR.

11. The method of claim 1, wherein the image data from the multiple images comprises consolidated pixel or patch data from multiple exposures.

12. The method of claim 1, wherein the convolutional neural network further outputs N'-class segmentation data.

13. The method of claim 1, wherein the convolutional neural network further comprises:
    a network branch including n-class output options for cap types.

14. A characterization method, comprising:
    capturing multiple images of a specimen container including a serum or plasma portion of a specimen;
    inputting image data from the multiple images to a convolutional neural network and processing the image data with the convolutional neural network; and
    outputting from the convolutional neural network a classification of the serum or plasma portion as being one or more of hemolytic, icteric, lipemic, and normal;
    wherein the convolutional neural network comprises an architecture including a deconvolution layer.

15. A characterization method, comprising:
    capturing multiple images of a specimen container including a serum or plasma portion of a specimen;
    inputting image data from the multiple images to a convolutional neural network and processing the image data with the convolutional neural network; and
    outputting from the convolutional neural network a classification of the serum or plasma portion as being one or more of hemolytic, icteric, lipemic, and normal;
    wherein the convolutional neural network comprises an architecture including a SoftMax layer.

16. A characterization method, comprising:
    capturing multiple images of a specimen container including a serum or plasma portion of a specimen;
    inputting image data from the multiple images to a convolutional neural network and processing the image data with the convolutional neural network; and
    outputting from the convolutional neural network a classification of the serum or plasma portion as being one or more of hemolytic, icteric, lipemic, and normal;
    wherein the classification of the serum or plasma portion comprises outputting a fine-grained index for one or more of hemolysis, icterus, and lipemia.

17. A characterization method, comprising:
    capturing multiple images of a specimen container including a serum or plasma portion of a specimen;
    inputting image data from the multiple images to a convolutional neural network and processing the image data with the convolutional neural network; and
    outputting from the convolutional neural network a classification of the serum or plasma portion as being one or more of hemolytic, icteric, lipemic, and normal;
    wherein the convolutional neural network comprises:
    a first network branch including N'-class segmentation outputs, and
    a second network branch including N-class output options classes for each of hemolytic, icteric, and lipemic.

18. A quality check module for pre-screening a specimen for presence of an interferent, comprising:
    an image capture device configured to capture multiple images of a specimen container containing a serum or plasma portion of a specimen; and
    a computer coupled to the image capture device, the computer configured and capable of being operated to:
    input image data from the multiple images to a convolutional neural network and process the image data with the convolutional neural network, the convolutional neural network comprising an architecture that includes a deconvolution layer, and
    output from the convolutional neural network a classification of the serum or plasma portion as being one or more of hemolytic, icteric, lipemic, and normal.

19. A specimen testing apparatus, comprising:
a track;
a carrier moveable on the track and configured to contain a specimen container containing a serum or plasma portion of a specimen;
image capture devices arranged around the track and configured to capture multiple images of a specimen container and the serum or plasma portion of the specimen from multiple viewpoints; and
a computer coupled to the image capture devices, the computer configured and capable of being operated to:
input image data from the multiple images to a convolutional neural network and process the image data with the convolutional neural network, the convolutional neural network comprising an architecture that includes a SoftMax layer, and
output from the convolutional neural network a classification of the serum or plasma portion as being one or more of hemolytic, icteric, lipemic, and normal.

* * * * *